United States Patent
Chen et al.

(10) Patent No.: US 7,402,603 B2
(45) Date of Patent: Jul. 22, 2008

(54) CYCLOOXYGENASE-2 INHIBITOR/HISTONE DEACETYLASE INHIBITOR COMBINATION

(75) Inventors: Ying-Nan Pan Chen, Parsippany, NJ (US); Peter Lassota, Succasunna, NJ (US); Alexander Wallace Wood, Ho Ho Kus, NJ (US)

(73) Assignee: Novartis AG, Basel (CH)

( * ) Notice: Subject to any disclaimer, the term of this patent is extended or adjusted under 35 U.S.C. 154(b) by 698 days.

(21) Appl. No.: 10/494,221

(22) PCT Filed: Nov. 5, 2002

(86) PCT No.: PCT/EP02/12343

§ 371 (c)(1),
(2), (4) Date: Sep. 15, 2004

(87) PCT Pub. No.: WO03/039599

PCT Pub. Date: May 15, 2003

(65) Prior Publication Data

US 2005/0032899 A1    Feb. 10, 2005

Related U.S. Application Data

(60) Provisional application No. 60/419,314, filed on Oct. 17, 2002, provisional application No. 60/333,016, filed on Nov. 6, 2001.

(51) Int. Cl.
*A61K 31/405* (2006.01)

(52) U.S. Cl. .................................................... 514/415

(58) Field of Classification Search ................. 514/406, 514/415
See application file for complete search history.

(56) References Cited

U.S. PATENT DOCUMENTS

6,291,523 B1 * 9/2001 Fujimoto et al. ............ 514/533
6,552,065 B2 * 4/2003 Remiszewski et al. ...... 514/416

OTHER PUBLICATIONS

Salih A.K. et al., "Breast cancer prevention: present and future," Cancer Treatment Reviews, vol. 27, pp. 261-273 (2001).
Fabian C. J. et al., "Beyond tamoxifen: New endpoints for breast cancer chemoprevention, new drugs for breast cancer prevention," Annals of the New York Academy of Sciences, vol. 952, pp. 44-59 (2001).

* cited by examiner

*Primary Examiner*—Ardin Marschel
*Assistant Examiner*—James D. Anderson
(74) *Attorney, Agent, or Firm*—Gregory C. Houghton; Lydia T. McNally; Oona A. Manzari

(57) ABSTRACT

The invention relates to a combination which comprises (a) a cyclooxygenase-2 inhibitor ("COX-2 inhibitor") and (b) a histone deacetylase inhibitor ("HDAI") for simultaneous, concurrent, separate or sequential use, especially for use in the treatment of pre-malignant colon lesions or a colon cancer or other malignancies in a mammal, particularly a human. The invention also relates to pharmaceutical compositions comprising such a combination and to a method of treating pre-malignant colon lesions (e.g. polyps) and colon cancer, as well as other malignancies, in a mammal, particularly a human, with such a combination. The present invention further also relates to a commercial package or product comprising such a combination.

1 Claim, No Drawings

CYCLOOXYGENASE-2 INHIBITOR/HISTONE DEACETYLASE INHIBITOR COMBINATION

The invention relates to a combination which comprises (a) a cyclooxygenase-2 inhibitor ("COX-2 inhibitor") and (b) a histone deacetylase Inhibitor ("HDAI") for simultaneous, concurrent, separate or sequential use, especially for use in the treatment of pre-malignant colon lesions or a colon cancer or other malignancies in a mammal, particularly a human. The invention also relates to pharmaceutical compositions comprising such a combination and to a method of treating pre-malignant colon lesions (e.g. polyps) and colon cancer, as well as other malignancies, in a mammal, particularly a human, with such a combination. The present invention further also relates to a commercial package or product comprising such a combination.

The COX-2 inhibitors used in the combination of the present invention are typically those which have an $IC_{50}$ for COX-2 inhibition of less than about 2 μM and an $IC_{50}$ for COX-1 inhibition of greater than about 5 μM, e.g. when measured in the assays described by Brideau et al., Inflamm. Res. 45:68-74 (1996). Preferably the COX-2 inhibitor has a selectivity ratio of at least 10, more preferably at least 40, for COX-2 inhibition over COX-1 inhibition.

Of the known COX-2 inhibitors, the 5-alkyl substituted 2-arylaminophenylacetic acids and derivatives are especially useful in the present invention. Such compounds, their use and preparation are disclosed in U.S. Pat. No. 6,291,523 and are herein incorporated by reference.

Useful COX-2 inhibitors disclosed in U.S. Pat. No. 6,291,523 are described by formula Ia

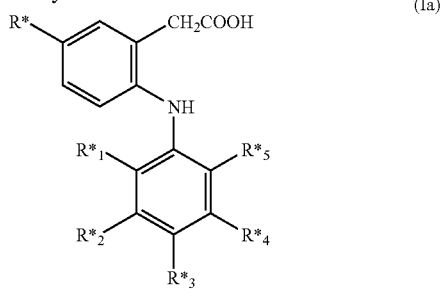

(Ia)

wherein
R* is methyl or ethyl;
$R^*_1$ is chloro or fluoro;
$R^*_2$ is hydrogen or fluoro;
$R^*_3$ is hydrogen, fluoro, chloro, methyl, ethyl, methoxy, ethoxy or hydroxy;
$R^*_4$ is hydrogen or fluoro; and
$R^*_5$ is chloro, fluoro, trifluoromethyl or methyl;
pharmaceutically acceptable salts or solvates thereof; and pharmaceutically acceptable prodrug esters thereof.

A particular embodiment of the invention relates to the compounds of formula Ia wherein R* is methyl or ethyl; $R^*_1$ is chloro or fluoro; $R^*_2$ is hydrogen; $R^*_3$ is hydrogen, fluoro, chloro, methyl or hydroxy; $R^*_4$ is hydrogen; and $R^*_5$ is chloro, fluoro or methyl; pharmaceutically acceptable salts thereof; and pharmaceutically acceptable prodrug esters thereof.

A preferred embodiment relates to the compounds of formula Ia wherein R* is methyl or ethyl; $R^*_1$ is fluoro; $R^*_2$ is hydrogen; $R^*_3$ is hydrogen, fluoro or hydroxy; $R^*_4$ is hydrogen; and $R^*_5$ is chloro; pharmaceutically acceptable salts thereof; and pharmaceutically acceptable prodrug esters thereof.

Another preferred embodiment of the invention relates to compound of formula Ia wherein R* is ethyl or methyl; $R^*_1$ is fluoro; $R^*_2$ is hydrogen or fluoro; $R^*_3$ is hydrogen, fluoro, ethoxy or hydroxy; $R^*_4$ is hydrogen or fluoro; and $R^*_5$ is chloro, fluoro or methyl; pharmaceutically acceptable salts thereof; and pharmaceutically acceptable prodrug esters thereof.

Further preferred are said compounds wherein R* is methyl or ethyl; $R^*_1$ is fluoro; $R^*_2$-$R^*_4$ are hydrogen or fluoro; and $R^*_5$ is chloro or fluoro; pharmaceutically acceptable salts thereof; and pharmaceutically acceptable prodrug esters thereof.

A further embodiment of the invention relates to the compounds of formula Ia wherein R* is methyl or ethyl; $R^*_1$ is fluoro; $R^*_2$ is fluoro; $R^*_3$ is hydrogen, ethoxy or hydroxy; $R^*_4$ is fluoro; and $R^*_5$ is fluoro; pharmaceutically acceptable salts thereof; and pharmaceutically acceptable prodrug esters thereof.

Another preferred embodiment of the invention relates to the compounds of formula Ia wherein R* is methyl; $R^*_1$ is fluoro; $R^*_2$ is hydrogen; $R^*_3$ is hydrogen or fluoro; $R^*_4$ is hydrogen; and $R^*_5$ is chloro; pharmaceutically acceptable salts thereof; and pharmaceutically acceptable prodrug esters thereof.

Particular embodiments of the invention relate to compounds of formula Ia
(a) wherein R* is methyl; $R^*_1$ is fluoro; $R^*_2$ is hydrogen; $R^*_3$ is hydrogen; $R^*_4$ is hydrogen; and $R^*_5$ is chloro; pharmaceutically acceptable salts thereof; and pharmaceutically acceptable prodrug esters thereof;
(b) wherein R* is methyl; $R^*_1$ is fluoro; $R^*_2$ is hydrogen; $R^*_3$ is fluoro; $R^*_4$ is hydrogen; and $R^*_5$ is chloro; pharmaceutically acceptable salts thereof; and pharmaceutically acceptable prodrug esters thereof;
(c) wherein R* is ethyl; $R^*_1$ is fluoro; $R^*_2$ is fluoro; $R^*_3$ is hydrogen; $R^*_4$ is fluoro; and $R^*_5$ is fluoro; pharmaceutically acceptable salts thereof; and pharmaceutically acceptable prodrug esters thereof; and
(d) wherein R* is ethyl; $R^*_1$ is chloro; $R^*_2$ is hydrogen; $R^*_3$ is chloro; $R^*_4$ is hydrogen; and $R^*_6$ is methyl; pharmaceutically acceptable salts thereof; and pharmaceutically acceptable prodrug esters thereof.

Pharmaceutically acceptable prodrug esters are ester derivatives which are convertible by solvolysis or under physiological conditions to the free carboxylic acids of formula Ia. Such esters are e.g. lower alkyl esters (such as the methyl or ethyl ester), carboxy-lower alkyl esters such as the carboxymethyl ester, nitrooxy-lower alkyl esters (such as the 4-nitrooxybutyl ester), and the like. Preferred are the 5-alkyl substituted 2-arylaminophenylacetoxyacetic acids of formula Ib

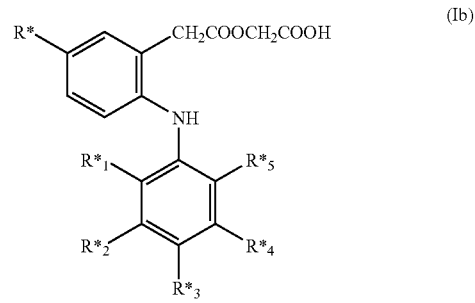

(Ib)

wherein R* and R*₁-R*₅ have meaning as defined hereinabove for compounds of formula Ia; and pharmaceutically acceptable salts thereof.

Thus, COX-2 inhibitors useful for use in the present invention are compounds of formula I

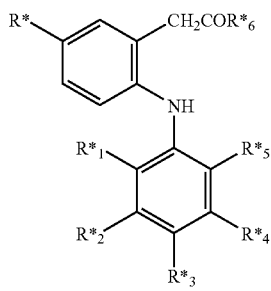

(I)

wherein
R* is methyl or ethyl;
R*₁ is chloro or fluoro;
R*₂ is hydrogen or fluoro;
R*₃ is hydrogen, fluoro, chloro, methyl, ethyl, methoxy, ethoxy or hydroxy;
R*₄ is hydrogen or fluoro;
R*₅ is chloro, fluoro, trifluoromethyl or methyl; and
R*₆ is hydroxy or —OCH₂COOH;

pharmaceutically acceptable salts or solvates thereof; and pharmaceutically acceptable prodrug esters thereof.

Pharmaceutically acceptable salts represent metal salts, such as alkaline metal salts, e.g. sodium, potassium, magnesium or calcium salts, as well as ammonium salts, which are formed e.g. with ammonia and mono- or di-alkylamines, such as diethylammonium salts, and with amino acids, such as arginine and histidine salts.

The compound 5-methyl-2-(2'-chloro-6'-fluoro-anilino)-phenyl acetic acid, as well as its pharmaceutically acceptable salts, is an especially useful COX-2 inhibitor for use in the present invention.

Also useful in the practice of the invention are the following COX-2-inhibiting compounds, derivatives thereof, or pharmaceutically acceptable salts thereof, or any hydrate thereof: rofecoxib, etoricoxib, celecoxib, valdecoxib, and parecoxib.

Another class of COX-2 inhibitors compounds for use in the invention is the methane sulfonanilide class of inhibitors, of which NS-398, flosulide, nimesulide and (i) are example members.

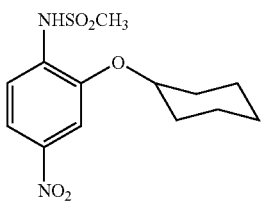

NS-398

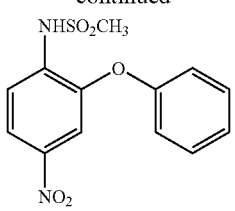

Nimesulide

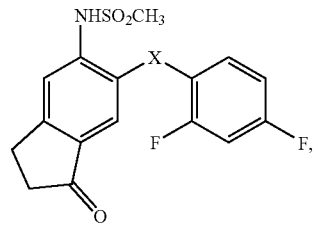

(i)

Flosulide

X = S
X = O

A further class of COX-2 inhibitors useful in the practice of the present invention is the tricyclic inhibitor class, which can be further divided into the sub-classes of tricyclic inhibitors with a central carbocyclic ring (examples include SC-57666, 1 and 2; those with a central monocyclic heterocyclic ring (examples include DuP697, SC-58125, SC-58635, SC-236 and 3, 4 and 5); and those with a central bicyclic heterocyclic ring (examples include 6, 7, 8, 9 and 10). Compounds 3, 4, and 5 are described in U.S. Pat. No. 5,474,995. The structure of the active agents identified hereinbefore or hereinafter by code nos., generic or trade names may be taken from the actual edition of the standard compendium "The Merck Index" or from databases, e.g. Patents International (e.g. IMS World Publications).

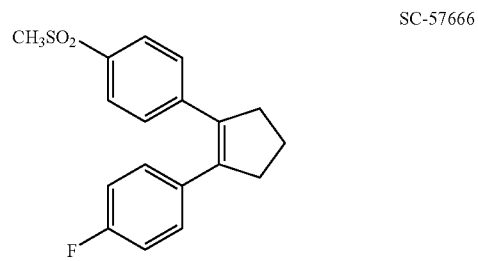

SC-57666

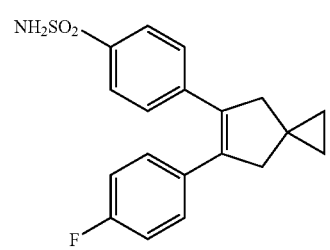

1

-continued
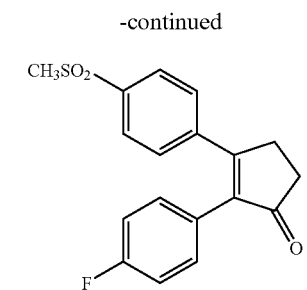
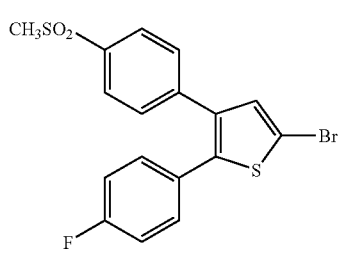
DuP697
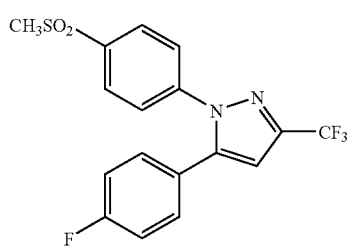
SC-58125
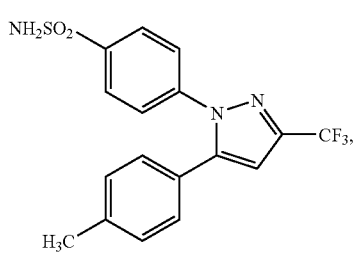
SC-58635
celecoxib
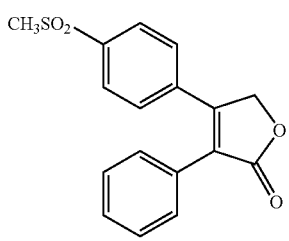
3
-continued
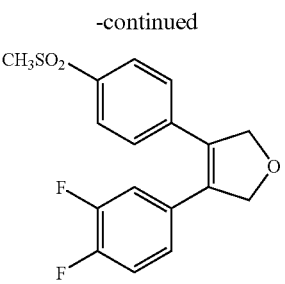
4
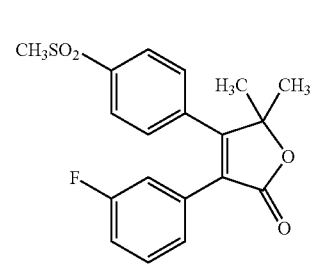
5
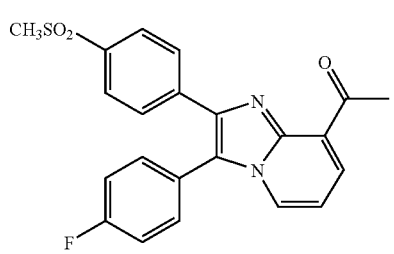
6
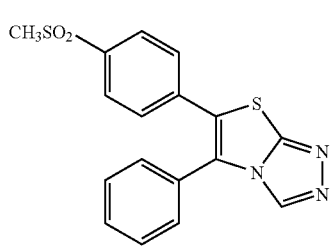
7
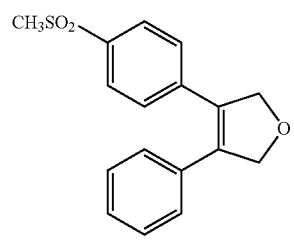
8
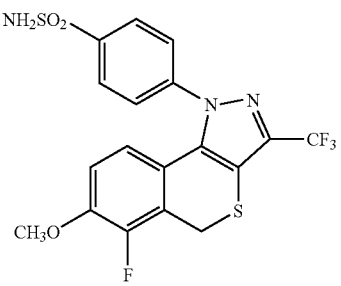
9

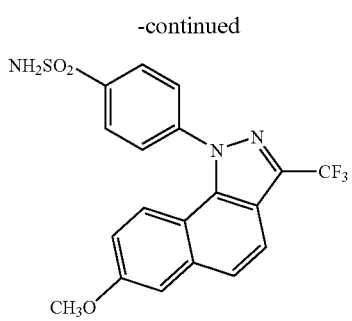

A yet further class of COX-2 inhibitors can be referred to as those which are structurally modified nonsteroidal antiinflammatory drugs (NSAIDs), and includes 11a and structure 11b as exemplary members. The synthesis of compound 11b is described in U.S. Pat. No. 5,622,948.

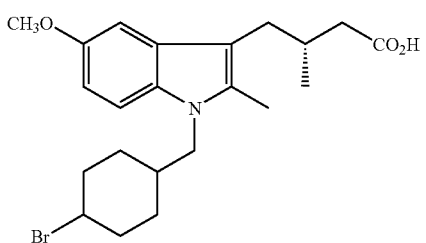

11a

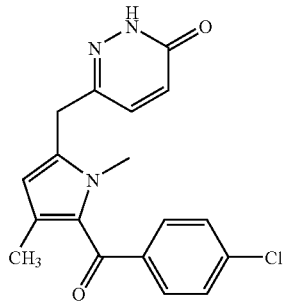

11b

In addition to these structural classes, sub-classes, and specific COX-2 inhibitor compound examples, examples of compounds which selectively inhibit cyclooxygenase-2 have also been described in the following patent publications and are herein incorporated by reference: U.S. Pat. Nos. 5,344,991, 5,380,738, 5,393,790, 5,409,944, 5,434,178, 5,436,265, 5,466,823, 5,474,995, 5,510,368, 5,536,752, 5,550,142, 5,552,422, 5,604,253, 5,604,260, 5,639,780; and International Patent Specification Nos. 94/13635, 94/15932, 94/20480, 94/26731, 94/27980, 95/00501, 95/15316, 96103387, 96/03388, 96/06840; and International Publication No.'s WO 94/20480, WO 96/21667, WO 96/31509, WO 96/36623, WO 97/14691, WO 97/16435.

Additional COX-2 inhibitor compounds, the use of which are included in the scope of this invention, include:

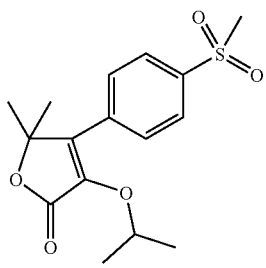

12

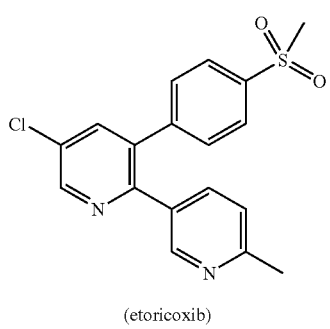

13

(etoricoxib)

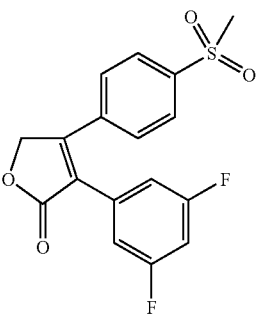

14

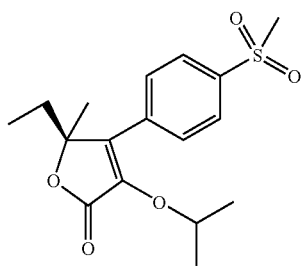

15

-continued

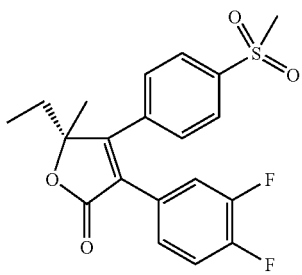
16

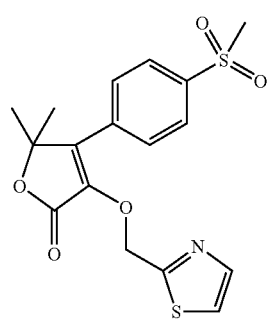
17

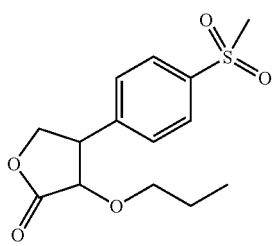
18

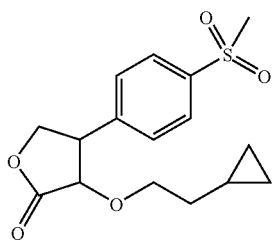
19

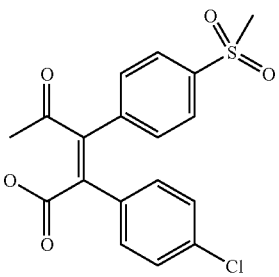
20

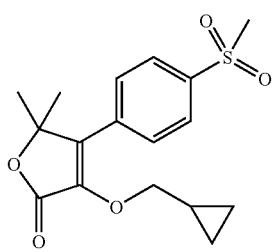
21

-continued

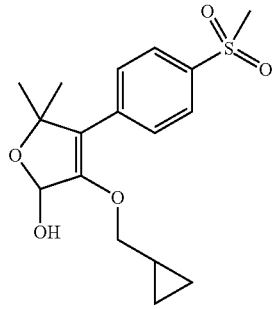
22

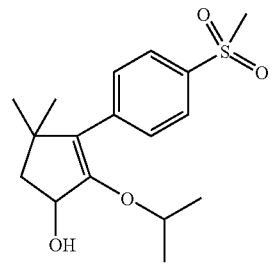
23

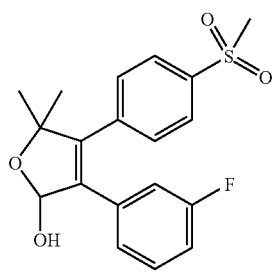
24

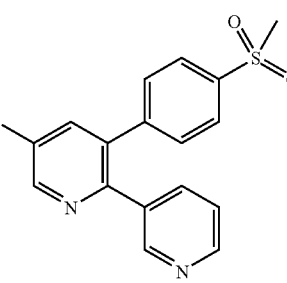
25

Some of the compounds above can also be identified by the following chemical names:
3: 3-phenyl-4-(4-(methylsulfonyl)phenyl)-2-(5H)-furanone;
4: 3-(3,4-difluorophenyl)4(4-(methylsulfonyl)phenyl)-2-(5H)-faranone;
5: 5,5-dimethyl-4-(4-(methylsulfonyl)phenyl)-3-(3-fluorophenyl)-H-furan-2-one;
12: 5,5-dimethyl-4-(4-(methylsulfonyl)phenyl)-3-(2-propoxy)5H-furan-2-one;
13: 5-chloro-3-(4-(methylsulfonyl)phenyl)-2-(2-methyl-5-pyridinyl)pyridine;
14: 2-(3,5-difluorophenyl-3-(4-(methylsulfonyl)phenyl)-2-cyclopenten-1-one;
15: 5(S)-5-ethyl-5-methyl-4-(4-methylsulfonyl)phenyl)-3-(2-propoxy)-5H-furan-2-one;
16: 5-ethyl-5-methyl-4-(4-(methylsulfonyl)phenyl)-3-(3,4-difluorophenyl)-5H-furan-2-one;
17: 3-((2-thiazolyl)methoxy)-4-(4-methylsulfonyl)phenyl)-5,5-dymethyl-5H-furan-2-one;

18: 3-propyloxy-4-(4-methylsulfonyl)phenyl)5,5-dimethyl-5H-furan-2-one;
19: 3-(1-cyclopropylethoxy)-5,5-dimethyl-4-(4-methylsulfonyl)phenyl)-5H-furan-2-one;
20: sodium 2-(4-chlorophenyl)-3-(4-methylsulfonyl)phenyl)$_4$-oxo-2-pentenoate;
21: 3-(cyclopropylmethoxy)-5,5-dimethyl-4-(4-methylsulfonyl)phenyl)-5H-furan-2-one;
22: 3-(cyclopropylmethoxy)5,5-dimethyl-4-(4-methylsulfonyl)phenyl)-2,5-dihydrofuran-2-ol;
23:3-isopropoxy-5,5-dimethyl-4-(4-methylsulfonyl)phenyl)-2,5-dihydrofuran-2-ol;
24: 5,5-dimethyl-3-(3-fluorophenyl)-2-hydroxy-4-(4-methylsulfonlyl)phenyl)-2,5-dihydrofuran;
25: 5-Chloro-3-(4-methylsulfonyl)phenyl)-2-(3-pyridinyl)pyridine.

The following publications describe and/or provide methods for making the compounds as indicated: compounds 12, 15, 17, 18, 19 and 21, WO 97/14691; compounds 22, 23 and 24, WO 97/16435; compound 20, WO 96/36623; compound 14, U.S. Pat. No. 5,536,752; compound 16, U.S. Pat. No. 5,474,995; compounds 13 and 25, WO 98/03484.

Also incorporated herein by reference are those compounds described in WO 96/41645 as having structural formula III, shown below, and the definition and preferred definitions and species described therein:

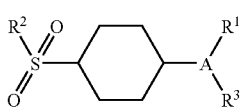

(III)

Particulary preferred compounds of formula (III) include:
5-(4-fluorophenyl)-[4-(methylsulfonyl)phenyl]-3-(trifluoromethyl)pyrazole;
4-(4-fluorophenyl)-5-[4-(methylsulfonyl)phenyl]-1-phenyl-3-(trifluoromethyl)pyrazole;
4-(5-(4-chlorophenyl)-3-(4-methodoxyphenyl)-1H-pyrazol-1-yl)benzenesulfonamide;
4-(3,5-bis(4-methylphenyl)-1H-pyrazol-1-yl)benzenesulfonamide;
4-(5-(4-chlorophenyl)$_3$-phenyl-1H-pyrazol-1-yl)benzenesulfonamide;
4-(3,5-bis(4-methoxyphenyl)-1H-pyrazol-1-yl)benzenesulfonamide;
4-(5-(4-chlorophenyl)-3-(4-methylphenyl)-1H-pyrazol-1-yl) benzenesulfonamide;
4-(5-(4-chlorophenyl)$_3$-(4-nitrophenyl)-1H-pyrazol-1-yl)benzenesulfonamide;
4-(5-(4-chlorophenyl)-3-(5-chloro-2-thienyl)-1H-pyrazol-1-yl)benzenesulfonamide;
4-(4-chloro-3,5-diphenyl-1H-pyrazol-1-yl)benzenesulfonamide;
4-(5-(4-chlorophenyl)-3-(trifluoromethyl)-1H-pyrazol-1-yl)benzenesulfonamide;
4-(5-phenyl)-3-(trifluoromethyl)-1H-pyrazol-1-yl)benzenesulfonamide;
4-(5-(4-fluorophenyl)-3-(trifluoromethyl)-1H-pyrazol-1-yl)benzenesulfonamide;
4-(5-(4-methoxyphenyl)-3-(trifluoromethyl)-1H-pyrazol-1-yl)benzenesulfonamide;
4-(5-(4-chlorophenyl)-3-(difluoromethyl)-1H-pyrazol-1-yl)benzenesulfonamide;
4-(5-(4-methylphenyl)-3-(trifluoromethyl)-1H-pyrazol-1-yl)benzenesulfonamide;
4-(4-chloro-5-(4-chlorophenyl)-3-(trifluoromethyl)1H-pyrazol-1-yl)benzenesulfonamide;
4-(3-(difluoromethyl)$_5$-(4-methylphenyl)-1H-pyrazol-1-yl)benzenesulfonamide;
4-(3-(difluoromethyl)-5-phenyl-1H-pyrazol-1-yl)benzenesulfonamide;
4-(3-(difluoromethyl)-5-(4-methoxyphenyl)-1H-pyrazol-1-yl)benzenesulfonamide;
4-(3-cyano-5-(4-fluorophenyl)-1H-pyrazol-1-yl)benzenesulfonamide;
4-(3-(difluoromethyl)$_5$-(3-fluoro-4-methodoxyphenyl)-1H-pyrazol-1-yl)benzenesulfonamide;
4-(5-(3-fluoro-4-methoxyphenyl)-3-(trifluoromethyl)-1H-pyrazol-1-yl)benzenesulfonamide;
4-(4-chloro-5-phenyl-1H-pyrazol-1-yl)benzenesulfonamide;
4-(5-(4-chlorophenyl)-3-hydroxyphenyl)-1H-pyrazol-1-yl)benzenesulfonamide;
4-(S-(N,N-dimethylamino)phenyl)-3-trifluormethyl)-1H-pyrazol-1-yl)benzenesulfonamide;
5-(4-fluorophenyl)-6-(4-(methylsulfonyl)phenyl)spiro[2.4]hept-5-ene;
4-(6-(4-fluorophenyl)spiro[2.4]hept-5-en-5-yl)benzenesulfonamide;
6-(4-fluorophenyl)-7-(4(methylsulfonyl)phenyl)spiro[3.4]octene;
5-(3-chloro-4-methoxyphenyl)-6-(4-(methylsulfonyl)phenyl)spiro[2.4]hept-5-ene;
4-(6-(3-chloro-4 methoxyphenyl)spiro[2.4]hept-5-en-5-yl)benzenesulfonamide;
5-(3,5-chloro 4-methodoxyphenyl)-6-(4-(methylsulfonyl)phenyl)spiro[2.4]hept-5-ene;
5-(3-chloro-4-fluorophenyl)-6-(4-(methylsulfonyl)phenyl)spiro[2.4]hept-5-ene;
4-(6-(3,4-dichlorophenyl)spiro[2.4]hept-5-en-5-yl)benzenesulfonamide;
2-(3-chloro-fluorophenyl)-4(4-fluorophenyl)-5-(4-methylsulfonylphenyl)thiazole;
2-(2-chlorophenyl)-4-(4-fluorophenyl)-5-(4-methylsulfonylphenyl)thiazole;
5-(4-fluorophenyl)-4-(4-methylsulfonylphenyl)-2-methylthiazole;
4-(4-fluorophenyl)-5-(4-methylsulfonylphenyl)-2-trifluoromethylthiazole;
4-(4-fluorophenyl)-5-(4-methylsulfonylphenyl)-2-(2-thienyl)thiazole;
4-(4-fluorophenyl)-5-(4-methylsulfonylphenyl)-2-benzenesulfonamide;
4-(4-fluorophenyl)-5-(4-methylsulfonylphenyl)-2-(1-propylamino)thiazole;
2-((3,5-dichlorophenoxy)methyl)-4-(4-fluorophenyl)-5-(4-(methylsulfonyl)phenyl)thiazole;
5-(4-fluorophenyl)(4-methylsulfonylphenyl)-2-trifluoromethylthiazole;
1-methylsulfonyl-4-(1,1-dimethyl-4-(4-fluorophenyl)cyclopenta-2,4-dien-3-yl)benzene;
4-(4-(4-fluorophenyl-1,1-dimethylcyclopenta-2,4-dien-3-yl)benzenesulfonamide;
5-(4-fluorophenyl)-6-(4-(methylsulfonyl)phenyl)spiro[2.4]hepta4,6-diene;
4-(6-(4-fluorophenyl)spiro[2.4]hepta-4,6-dien-5-yl)benzenesulfonamide;
6-(4-fluorophenyl)-2-methoxy-5-(4-(methylsulfonyl)phenyl)-pyridine-3-carbonitrile;
2-bromo-6-(4-fluorophenyl)-5-(4-(methylsulfonyl)phenyl)pyridine-3-carbonitrile;

6-(4-fluorophenyl)-5-(4-(methylsulfonyl)phenyl)-2-phenyl-pyridine-3-carbonitrile;
4-(2-(4-methylpyridin-2-yl)-4-(trifluoromethyl)-1H-imidazol-1-yl)benzenesulfonamide;
4-(2-(5-methylpyridin-3-yl)-4-(trifluoromethyl)-1H-imidazol-1-yl)benzenesulfonamide;
4-(2-(2-methylpyridin-3-yl)-(trifluoromethyl)-1H-imidazol-1-yl)benzenesulfonamide;
3-(1-(4-(methylsulfonyl)phenyl)-4-(trifluoromethyl)-1H-imidazol-2-yl)benzenesulfonamide;
2-(1-(4-(methylsulfonyl)phenyl)-4-(trifluoromethyl)-1H-imidazol-2-yl)pyridine;
2-methyl-4-(1-(4-(methylsulfonyl)phenyl)-4-(trifluoromethyl)-1H-imidazol-2-yl)pyridine;
2-methyl-6-(1-(4-(methylsulfonyl)phenyl)-4-(trifluoromethyl)-1H-imidazole-2-yl)pyridine;
4(2-(6-methylpyridin-3-yl)-4-(trifluoromethyl)-1H-imidazol-1-yl)benzenesulfonamide;
2-(3,4-difluorophenyl)-1-(4-(methylsulfonyl)phenyl)-4-(trifluoromethyl)-1H-imidazole;
4(2-(4-methylphenyl)$_4$-(trifluoromethyl)-1H-imidazol-1-yl)benzesulfonamide;
2-(4-chlorophenyl)-1-(4-(methylsulfonyl)phenyl)-4-methyl-1H-imidazole;
2-(4-chlorophenyl)-1-(4(methylsulfonyl)phenyl)-4-phenyl-1H-imidazole;
2-(4-chlorophenyl)-4-(4-fluorophenyl)-1-(4-(methylsulfonyl)phenyl)-1H-imidazole;
2-(3-fluoro-4-methoxyphenyl)-1-(4-(methylsulfonyl)phenyl)-4(trifluoromethyl)-1H-imidazole;
1-(4-methylsulfonyl)phenyl)-2-phenyl-4-trifluoromethyl-1H-imidazole;
2-(4-methylphenyl)-1-(4-(methylsulfonyl)phenyl)trifluoromethyl-1H-imidazole;
4-(2-(3-chloro-4-methylphenyl)-4-(trifluoromethyl-1H-Imidazol-1-yl)benzenesulfonamide;
2-(3-fluoro-5-methylphenyl)-1-(4-methylsulfonyl)phenyl)-4(trifluoromethyl)-1H-imidazole;
4-(2-(3-fluoro-5-methylphenyl)$_4$(trifluoromethyl)-1H-imidazol-1-yl)benzenesulfonamide;
2-(3-methylphenyl)-1-(4-(methylsulfonyl)phenyl)-4(trifluoromethyl)-1H-imidazole;
4-(2-(3-methylphenyl)-4-(trifluoromethyl)-1H-imidazol-1-yl)benzenesulfonamide;
1-(4-(methylsulfonyl)phenyl)-2-(3-chlorophenyl)-4-(trifluoromethyl)1H-imidazole;
4-(2-(3-chlorophenyl)-4-(trifluoromethyl)-1H-imidazol-1-yl)benzenesulfonamide;
4-(2-phenyl-4-(trifluoromethyl)-1H-imidazol-1-yl)benzenesulfonamide;
4-(2-(4-methodoxy-3-chlorophenyl)-4-(trifluoromethyl)1H-imidazol-1-yl) benzenesulfonamide;
1-allyl-4-(4-fluorophenyl)-3-(4-(methylsulfonyl)phenyl)-5-(trifluoromethyl)1H-pyrazole;
4-(1-ethyl-4-(4-fluorophenyl)-5-(trifluoromethyl)-1H-pyrazol-3-yl)benzenesulfonamide;
N-phenyl-(4(4-fluorophenyl)$_3$-(4-(methylsulfonyl)phenyl)-5-(trifluoromethyl)-1H-pyrazol-1-yl)acetamide;
ethyl (4-(4-fluorophenyl)-3-(4-(methylsulfonyl)phenyl)-5-(trifluoromethyl)-1H-pyrazol-1-yl)acetate;
4-(4-fluorophenyl)-3-(4-methylsulfonyl)phenyl)-1-(2-phenylethyl)-1H-pyrazole;
4-(4-fluorophenyl)-3(4-methylsulfonyl)phenyl)-1-(2-phenylethyl)-5-(trifluoromethyl)pyrazole;
1-ethyl-4-(4-fluorophenyl)-3-(4-(methylsulfonyl)phenyl)-5-(trifluoromethyl)-1H-pyrazole;
5(4-fluorophenyl)-4(4-methylsulfonyl)phenyl)-2-(trifluoromethyl)-1H-imidazole;
4-(4-methylsulfonyl)phenyl)-5-(2-thiophenyl)-2-(trifluoromethyl)-1H-imidazole;
5(4-fluorophenyl)-2-methodoxy-4-(methylsulfonyl)phenyl)-6-(trifluoromethyl)pyridine;
2-ethoxy(4-fluorophenyl)-(4-(methylsulfonyl)phenyl-6-(trifluoromethyl)pyridine;
1-(4-fluorophenyl)-4-(4(methylsulfonyl)phenyl)-2-(2-propynyloxy)-(trifluoromethyl)pyridine;
2-bromo-5-(4-fluorophenyl-4-(4-(methylsulfonyl)phenyl)-6-(trifluoromethyl)pyridine;
4-(2-(3-chloro-methoxyphenyl-4,5-difluorophenyl)benzensulfonamide;
1-(4-fluorophenyl)-2-(4-(methylsulfonyl)phenyl)benzene;
5-difluoromethyl-(4-(methylsulfonyl)phenyl)-3-phenylisoxazole;
4-(3-ethyl-5-phenylisoxazol-4-yl)benzensulfonamide;
4(5-difluoromethyl-3-phenylisoxazolyl)benzenesulfonamide;
4(5-hydroxymethyl-3-phenylisoxazol-4-yl)benzenesulfonamide;
4(5-methyl-3-phenylisoxazolyl)benzenesulfonamide;
1-(2-(4-fluorophenyl)cyclopenten-1-yl)-4-(methylsulfonyl)benzene;
1-(2-(4-fluoro-2-methylphenyl)cyclopenten-1-yl)-4-(methylsulfonyl)benzene;
1-(2-(4-chlorophenyl)cyclopenten-1-yl)-(methylsulfonyl)benzene;
1-(2-(2,4-dichlorophenyl)cyclopenten-1-yl)-4-(methylsulfonyl)benzene;
1-(2-(4-trifluoromethylphenyl)cyclopenten-1-yl)-4-(methylsulfonyl)benzene;
1-(2-(4-methylthiophenyl)cyclopenten-1-yl)-4-(methylsulfonyl)benzene;
1-(2-(4-fluorophenyl)4,4-dimethylcyclopenten-1-yl)-4-(methylsulfonyl)benzene;
4-(2-(4-fluorophenyl)4,4-dimethylcyclopenten-1-yl)benzesulfonamide;
1-(2-(4-chlorophenyl)4,4-dimethylcyclopenten-1-yl)-4(methylsulfonyl)benzene;
4-(2-(4-chlororophenyl)-4,4-dimethylcyclopenten-1-yl)benzenesulfonamide;
4-(2-(4-fluorophenyl)cyclopenten-1-yl)benzenesulfonamide;
4-(2-(4-chlorophenyl)cyclopenten-1-yl)benzenesulfonamide;
1-(2-(4-methoxyphenyl)cyclopenten-1-yl)-4-(methylsulfonyl)benzene;
1-(2-(2,3-difluorophenyl)cyclopenten-1-yl)-4-(methylsulfonyl)benzene;
4-(2-(3-fluoro-4-methodyphenyl)cyclopenten-1-yl)benzenesulfonamide;
1-(2-(3-chloro-4-methoxyphenyl)cyclopenten-1-yl)-4-(methylsulfonyl)benzene;
4-(2-(3-chloro-4-fluorophenyl)cyclopenten-1-yl-benzenesulfonamide;
4-(2-(2-methylpyridin-5-yl)cyclopenten-1-yl)benzenesulfonamide;
ethyl 2-(4-(4-fluorophenyl)-5-(4-methylsulfonyl)phenyl)oxazole-2-yl)-2-benzyl-acetate;
2-(4-(4-fluorophenyl)-5-(4-(methylsulfonyl)phenyl)oxazole-2-yl)acetic acid;
2-(tert-butyl)-4(4-fluorophenyl)-5-(4-methylsulfonyl)phenyl)oxazole;
4-(4-fluorophenyl)-5(4-(methylsulfonyl)phenyl)-2-phenyloxazole;

4-(4-fluorophenyl)-2-methyl-5-(4-methylsulfonyl)phenyl) oxazole; and 4-(5(3-fluoro-4-methoxyphenyl)-2-trifluoromethyl-4-oxazolyl)benzenesulfonamide;

or a pharmaceutically acceptable salt thereof.

HDAI compounds that are of particular interest for use in the combinations and methods of the invention are hydroxamate compounds described by the formula II

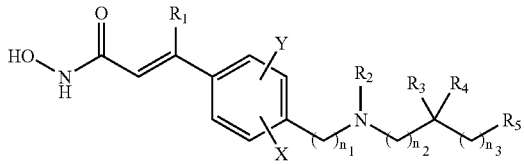

(II)

wherein $R_1$ is H, halo, or a straight chain $C_1$-$C_6$ alkyl (especially methyl, ethyl or n-propyl, which methyl, ethyl and n-propyl substituents are unsubstituted or substituted by one or more substituents described below for alkyl substituents);

$R_2$ is selected from H, $C_1$-$C_{10}$ alkyl, (preferably $C_1$-$C_6$ alkyl, e.g. methyl, ethyl or —$CH_2CH_2$—OH), $C_4$-$C_9$ cycloalkyl, $C_4$-$C_9$ heterocycloalkyl, $C_4$-$C_9$ heterocycloalkylalkyl, cycloalkylalkyl (e.g., cyclopropylmethyl), aryl, heteroaryl, arylalkyl (e.g. benzyl), heteroarylalkyl (e.g. pyridylmethyl), —$(CH_2)_n C(O)R_6$, —$(CH_2)_n OC(O)R_6$, amino acyl, HON—C(O)—CH=C($R_1$)-aryl-alkyl- and —$(CH_2)_n R_7$;

$R_3$ and $R_4$ are the same or different and independently H, $C_1$-$C_6$ alkyl, acyl or acylamino, or $R_3$ and $R_4$ together with the carbon to which they are bound represent C=O, C=S, or C=$NR_8$, or $R_2$ together with the nitrogen to which it is bound and $R_3$ together with the carbon to which it is bound can form a $C_4$-$C_9$ heterocycloalkyl, a heteroaryl, a polyheteroaryl, a non-aromatic polyheterocycle, or a mixed aryl and non-aryl polyheterocycle ring;

$R_5$ is selected from H, $C_1$-$C_6$ alkyl, $C_4$-$C_9$ cycloalkyl, $C_4$-$C_9$ heterocycloalkyl, acyl, aryl, heteroaryl, arylalkyl (e.g. benzyl), heteroarylalkyl (e.g. pyridylmethyl), aromatic polycycles, non-aromatic polycycles, mixed aryl and non-aryl polycycles, polyheteroaryl, non-aromatic polyheterocycles, and mixed aryl and non-aryl polyheterocycles;

n, $n_1$, $n_2$ and $n_3$ are the same or different and independently selected from 0-6, when $n_1$ is 1-6, each carbon atom can be optionally and independently substituted with $R_3$ and/or $R_4$;

X and Y are the same or different and independently selected from H, halo, $C_1$-$C_4$ alkyl, such as $CH_3$ and $CF_3$, $NO_2$, $C(O)R_1$, $OR_9$, $SR_9$, CN, and $NR_{10}R_{11}$;

$R_6$ is selected from H, $C_1$-$C_6$ alkyl, $C_4$-$C_9$ cycloalkyl, $C_4$-$C_9$ heterocycloalkyl, cycloalkylalkyl (e.g., cyclopropylmethyl), aryl, heteroaryl, arylalkyl (e.g., benzyl, 2-phenylethenyl), heteroarylalkyl (e.g., pyridylmethyl), $OR_{12}$, and $NR_{13}R_{14}$;

$R_7$ is selected from $OR_{15}$, $SR_{15}$, $S(O)R_{16}$, $SO_2R_{17}$, $NR_{13}R_{14}$, and $NR_{12}SO_2R_6$;

$R_8$ is selected from H, $OR_{15}$, $NR_{13}R_{14}$, $C_1$-$C_6$ alkyl, $C_4$-$C_9$ cycloalkyl, $C_4$-$C_9$ heterocycloalkyl, aryl, heteroaryl, arylalkyl (e.g., benzyl), and heteroarylalkyl (e.g., pyridylmethyl);

$R_9$ is selected from $C_1$-$C_4$ alkyl, for example, $CH_3$ and $CF_3$, C(O)-alkyl, for example C(O)$CH_3$, and C(O)$CF_3$;

$R_{10}$ and $R_{11}$ are the same or different and independently selected from H, $C_1$-$C_4$ alkyl, and —C(O)-alkyl;

$R_{12}$ is selected from H, $C_1$-$C_6$ alkyl, $C_4$-$C_9$ cycloalkyl, $C_4$-$C_9$ heterocycloalkyl, $C_4$-$C_9$ heterocycloalkylalkyl, aryl, mixed aryl and non-aryl polycycle, heteroaryl, arylalkyl (e.g., benzyl), and heteroarylalkyl (e.g., pyridylmethyl);

$R_{13}$ and $R_{14}$ are the same or different and independently selected from H, $C_1$-$C_6$ alkyl, $C_4$-$C_9$ cycloalkyl, $C_4$-$C_9$ heterocycloalkyl, aryl, heteroaryl, arylalkyl (e.g., benzyl), heteroarylalkyl (e.g., pyridylmethyl), amino acyl, or $R_{13}$ and $R_{14}$ together with the nitrogen to which they are bound are $C_4$-$C_9$ heterocycloalkyl, heteroaryl, polyheteroaryl, non-aromatic polyheterocycle or mixed aryl and non-aryl polyheterocycle;

$R_{15}$ is selected from H, $C_1$-$C_6$ alkyl, $C_4$-$C_9$ cycloalkyl, $C_4$-$C_9$ heterocycloalkyl, aryl, heteroaryl, arylalkyl, heteroarylalkyl and $(CH_2)_m ZR_{12}$;

$R_{16}$ is selected from $C_1$-$C_8$ alkyl, $C_4$-$C_9$ cycloalkyl, $C_4$-$C_9$ heterocycloalkyl, aryl, heteroaryl, polyheteroaryl, arylalkyl, heteroarylalkyl and $(CH_2)_m ZR_{12}$;

$R_{17}$ is selected from $C_1$-$C_6$ alkyl, $C_4$-$C_9$ cycloalkyl, $C_4$-$C_9$ heterocycloalkyl, aryl, aromatic polycycles, heteroaryl, arylalkyl, heteroarylalkyl, polyheteroaryl and $NR_{13}R_{14}$;

m is an integer selected from 0 to 6; and

Z is selected from O, $NR_{13}$, S and S(O), or a pharmaceutically acceptable salt thereof.

As appropriate, unsubstituted means that there is no substituent or that the only substituents are hydrogen.

Halo substituents are selected from fluoro, chloro, bromo and iodo, preferably fluoro or chloro.

Alkyl substituents include straight and branched $C_1$-$C_6$alkyl, unless otherwise noted.

Examples of suitable straight and branched $C_1$-$C_6$alkyl substituents include methyl, ethyl, n-propyl, 2-propyl, n-butyl, sec-butyl, t-butyl, and the like. Unless otherwise noted, the alkyl substituents include both unsubstituted alkyl groups and alkyl groups that are substituted by one or more suitable substituents, including unsaturation (i.e. there are one or more double or triple C—C bonds), acyl, cycloalkyl, halo, oxyalkyl, alkylamino, aminoalkyl, acylamino and $OR_{15}$, for example, alkoxy. Preferred substituents for alkyl groups include halo, hydroxy, alkoxy, oxyalkyl, alkylamino, and aminoalkyl.

Cycloalkyl substituents include $C_3$-$C_9$ cycloalkyl groups, such as cyclopropyl, cyclobutyl, cyclopentyl, cyclohexyl and the like, unless otherwise specified. Unless otherwise noted, cycloalkyl substituents include both unsubstituted cycloalkyl groups and cycloalkyl groups that are substituted by one or more suitable substituents, including $C_1$-$C_6$ alkyl, halo, hydroxy, aminoalkyl, oxyalkyl, alkylamino, and $OR_{15}$, such as alkoxy. Preferred substituents for cycloalkyl groups include halo, hydroxy, alkoxy, oxyalkyl, alkylamino and aminoalkyl.

The above discussion of alkyl and cycloalkyl substituents also applies to the alkyl portions of other substituents, such as without limitation, alkoxy, alkyl amines, alkyl ketones, arylalkyl, heteroarylalkyl, alkylsulfonyl and alkyl ester substituents and the like.

Heterocycloalkyl substituents include 3 to 9 membered aliphatic rings, such as 4 to 7 membered aliphatic rings, containing from one to three heteroatoms selected from nitrogen, sulfur, oxygen. Examples of suitable heterocycloalkyl substituents include pyrrolidyl, tetrahydrofuryl, tetrahydrothiofuranyl, piperidyl, piperazyl, tetrahydropyranyl, morphilino, 1,3-diazapane, 1,4-diazapane, 1,4-oxazepane, and 1,4-oxathiapane. Unless otherwise noted, the rings are unsubstituted or substituted on the carbon atoms by one or more suitable substituents, including $C_1$-$C_6$ alkyl, $C_4$-$C_9$ cycloalkyl, aryl, heteroaryl, arylalkyl (e.g., benzyl), and heteroarylalkyl (e.g., pyridylmethyl), halo, amino, alkyl amino and $OR_{15}$, for example alkoxy. Unless otherwise noted, nitrogen heteroatoms are unsubstituted or substituted by H, $C_1$-$C_4$ alkyl, arylalkyl (e.g., benzyl), and heteroarylalkyl (e.g., pyridylmethyl), acyl, aminoacyl, alkylsulfonyl, and arylsulfonyl.

Cycloalkylalkyl substituents include compounds of the formula —$(CH_2)_{n5}$-cycloalkyl wherein n5 is a number from 1-6. Suitable alkylcycloalkyl substituents include cyclopentylmethyl-, cyclopentylethyl, cyclohexylmethyl and the like. Such substituents are unsubstituted or substituted in the alkyl portion or in the cycloalkyl portion by a suitable substituent, including those listed above for alkyl and cycloalkyl.

Aryl substituents include unsubstituted phenyl and phenyl substituted by one or more suitable substituents, including $C_1$-$C_6$ alkyl, cycloalkylalkyl (e.g., cyclopropylmethyl), O(CO)alkyl, oxyalkyl, halo, nitro, amino, alkylamino, aminoalkyl, alkyl ketones, nitrile, carboxyalkyl, alkylsulfonyl, aminosulfonyl, arylsulfonyl, and $OR_{15}$, such as alkoxy. Preferred substituents include including $C_1$-$C_6$ alkyl, cycloalkyl (e.g., cyclopropylmethyl), alkoxy, oxyalkyl, halo, nitro, amino, alkylamino, aminoalkyl, alkyl ketones, nitrile, carboxyalkyl, alkylsulfonyl, arylsulfonyl, and aminosulfonyl. Examples of suitable aryl groups include $C_1$-$C_4$alkylphenyl, $C_1$-$C_4$alkoxyphenyl, trifluoromethylphenyl, methoxyphenyl, hydroxyethylphenyl, dimethylaminophenyl, aminopropylphenyl, carbethoxyphenyl, methanesulfonylphenyl and tolylsulfonylphenyl.

Aromatic polycycles include naphthyl, and naphthyl substituted by one or more suitable substituents, including $C_1$-$C_6$ alkyl, alkylcycloalkyl (e.g., cyclopropylmethyl), oxyalkyl, halo, nitro, amino, alkylamino, aminoalkyl, alkyl ketones, nitrile, carboxyalkyl, alkylsulfonyl, arylsulfonyl, aminosulfonyl and $OR_{15}$, such as alkoxy.

Heteroaryl substituents include compounds with a 5 to 7 member aromatic ring containing one or more heteroatoms, for example from 1 to 4 heteroatoms, selected from N, O and S. Typical heteroaryl substituents include furyl, thienyl, pyrrole, pyrazole, triazole, thiazole, oxazole, pyridine, pyrimidine, isoxazolyl, pyrazine and the like. Unless otherwise noted, heteroaryl substituents are unsubstituted or substituted on a carbon atom by one or more suitable substituents, including alkyl, the alkyl substituents identified above, and another heteroaryl substituent. Nitrogen atoms are unsubstituted or substituted, for example by $R_{13}$; especially useful N substituents include H, $C_1$-$C_4$ alkyl, acyl, aminoacyl, and sulfonyl.

Arylalkyl substituents include groups of the formula —$(CH_2)_{n5}$-aryl, —$(CH_2)_{n5}$—(CHaryl)-$(CH_2)_{n5}$-aryl or —$(CH_2)_{n5-1}$CH(aryl)(aryl) wherein aryl and n5 are defined above.

Such arylalkyl substituents include benzyl, 2-phenylethyl, 1-phenylethyl, tolyl-3-propyl, 2-phenylpropyl, diphenylmethyl, 2-diphenylethyl, 5,5-dimethyl-3-phenylpentyl and the like. Arylalkyl substituents are unsubstituted or substituted in the alkyl moiety or the aryl moiety or both as described above for alkyl and aryl substituents.

Heteroarylalkyl substituents include groups of the formula —$(CH_2)_{n5}$-heteroaryl wherein heteroaryl and n5 are defined above and the bridging group is linked to a carbon or a nitrogen of the heteroaryl portion, such as 2-, 3- or 4-pyridylmethyl, imidazolylmethyl, quinolylethyl, and pyrrolylbutyl. Heteroaryl substituents are unsubstituted or substituted as discussed above for heteroaryl and alkyl substituents.

Amino acyl substituents include groups of the formula —C(O)—$(CH_2)_n$—C(H)($NR_{13}R_{14}$)—$(CH_2)_n$—$R_5$ wherein n, $R_{13}$, $R_{14}$ and $R_5$ are described above. Suitable aminoacyl substituents include natural and non-natural amino acids such as glycinyl, D-tryptophanyl, L-lysinyl, D- or L-homoserinyl, 4-aminobutryic acyl, ±-3-amin-4-hexenoyl.

Non-aromatic polycycle substituents include bicyclic and tricyclic fused ring systems where each ring can be 4-9 membered and each ring can contain zero, 1 or more double and/or triple bonds. Suitable examples of non-aromatic polycycles include decalin, octahydroindene, perhydrobenzocycloheptene, perhydrobenzo-[f]-azulene. Such substituents are unsubstituted or substituted as described above for cycloalkyl groups.

Mixed aryl and non-aryl polycycle substituents include bicyclic and tricyclic fused ring systems where each ring can be 4-9 membered and at least one ring is aromatic. Suitable examples of mixed aryl and non-aryl polycycles include methylenedioxyphenyl, bis-methylenedioxyphenyl, 1,2,3,4-tetrahydronaphthalene, dibenzosuberane, dihydroanthracene, 9H-fluorene. Such substituents are unsubstituted or substituted by nitro or as described above for cycloalkyl groups.

Polyheteroaryl substituents include bicyclic and tricyclic fused ring systems where each ring can independently be 5 or 6 membered and contain one or more heteroatom, for example, 1, 2, 3, or 4 heteroatoms, chosen from O, N or S such that the fused ring system is aromatic. Suitable examples of polyheteroaryl ring systems include quinoline, isoquinoline, pyridopyrazine, pyrrolopyridine, furopyridine, indole, benzofuran, benzothiofuran, benzindole, benzoxazole, pyrroloquinoline, and the like. Unless otherwise noted, polyheteroaryl substituents are unsubstituted or substituted on a carbon atom by one or more suitable substituents, including alkyl, the alkyl substituents identified above and a substituent of the formula —O—($CH_2CH$=$CH(CH_3)(CH_2)$)$_{1-3}$H. Nitrogen atoms are unsubstituted or substituted, for example by $R_{13}$; especially useful N substituents include H, $C_1$-$C_4$ alkyl, acyl, aminoacyl, and sulfonyl.

Non-aromatic polyheterocyclic substituents include bicyclic and tricyclic fused ring systems where each ring can be 4-9 membered, contain one or more heteroatom, for example, 1, 2, 3, or 4 heteroatoms, chosen from O, N or S and contain zero or one or more C—C double or triple bonds. Suitable examples of non-aromatic polyheterocycles include hexitol, cis-perhydro-cyclohepta[b]pyridinyl, decahydro-benzo[f][1,4]oxazepinyl, 2,8 dioxabicyclo[3.3.0]octane, hexahydro-thieno[3,2-b]thiophene, perhydropyrrolo[3,2-b]pyrrole, perhydronaphthyridine, perhydro-1H-dicyclopenta[b,e]pyran. Unless otherwise noted, non-aromatic polyheterocyclic substituents are unsubstituted or substituted on a carbon atom by one or more substituents, including alkyl and the alkyl substituents identified above.

Nitrogen atoms are unsubstituted or substituted, for example, by $R_{13}$; especially useful N substituents include H, $C_1$-$C_4$ alkyl, acyl, aminoacyl, and sulfonyl.

Mixed aryl and non-aryl polyheterocycles substituents include bicyclic and tricyclic fused ring systems where each ring can be 4-9 membered, contain one or more heteroatom chosen from O, N or S, and at least one of the rings must be aromatic. Suitable examples of mixed aryl and non-aryl polyheterocycles include 2,3-dihydroindole, 1,2,3,4-tetrahydroquinoline, 5,11-dihydro-10H-dibenz[b,e][1,4]diazepine, 5H-dibenzo[b,e][1,4]diazepine, 1,2-dihydropyrrolo[3,4-b][1,5]benzodiazepine, 1,5-dihydro-pyrido[2,3-b][1,4]diazepin-4-one, 1,2,3,4,6,11-hexahydro-benzo[b]pyrido[2,3-e][1,4]diazepin-5-one. Unless otherwise noted, mixed aryl and non-aryl polyheterocyclic substituents are unsubstituted or substituted on a carbon atom by one or more suitable substituents, including, —N—OH, =N—OH, alkyl and the alkyl substituents identified above. Nitrogen atoms are unsubstituted or substituted, for example, by $R_{13}$; especially useful N substituents include H, $C_1$-$C_4$ alkyl, acyl, aminoacyl, and sulfonyl.

Amino substituents include primary, secondary and tertiary amines and in salt form, quaternary amines. Examples of amino substituents include mono- and di-alkylamino, mono- and di-aryl amino, mono- and di-arylalkyl amino, aryl-arylalkylamino, alkyl-arylamino, alkyl-arylalkylamino and the like.

Sulfonyl substituents include alkylsulfonyl and arylsulfonyl, for example methane sulfonyl, benzene sulfonyl, tosyl and the like.

Acyl substituents include groups of formula —C(O)—W, —OC(O)—W, —C(O)—O—W or —C(O)$NR_{13}R_{14}$, where W is $R_{16}$, H or cycloalkylalkyl.

Acylamino substituents include substituents of the formula —N($R_{12}$)C(O)—W, —N($R_{12}$)C(O)—O—W, and —N($R_{12}$)C(O)—NHOH and $R_{12}$ and W are defined above.

The $R_2$ substituent HON—C(O)—CH=C($R_1$)-aryl-alkyl- is a group of the formula

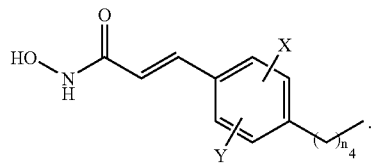

Preferences for each of the substituents include the following:

$R_1$ is H, halo, or a straight chain $C_1$-$C_4$ alkyl;

$R_2$ is selected from H, $C_1$-$C_6$ alkyl, $C_4$-$C_9$ cycloalkyl, $C_4$-$C_9$ heterocycloalkyl, alkylcycloalkyl, aryl, heteroaryl, arylalkyl, heteroarylalkyl, —$(CH_2)_nC(O)R_6$, amino acyl, and —$(CH_2)_nR_7$;

$R_3$ and $R_4$ are the same or different and independently selected from H, and $C_1$-$C_6$ alkyl, or $R_3$ and $R_4$ together with the carbon to which they are bound represent C=O, C=S, or C=$NR_8$;

$R_5$ is selected from H, $C_1$-$C_6$ alkyl, $C_4$-$C_9$ cycloalkyl, $C_4$-$C_9$ heterocycloalkyl, aryl, heteroaryl, arylalkyl, heteroarylalkyl, a aromatic polycycle, a non-aromatic polycycle, a mixed aryl and non-aryl polycycle, polyheteroaryl, a non-aromatic polyheterocycle, and a mixed aryl and non-aryl polyheterocycle;

n, $n_1$, $n_2$ and $n_3$ are the same or different and independently selected from 0-6, when $n_1$ is 1-6, each carbon atom is unsubstituted or independently substituted with $R_3$ and/or $R_4$;

X and Y are the same or different and independently selected from H, halo, $C_1$-$C_4$ alkyl, $CF_3$, $NO_2$, C(O)$R_1$, $OR_9$, $SR_9$, CN, and $NR_{10}R_{11}$;

$R_6$ is selected from H, $C_1$-$C_6$ alkyl, $C_4$-$C_9$ cycloalkyl, $C_4$-$C_9$ heterocycloalkyl, alkylcycloalkyl, aryl, heteroaryl, arylalkyl, heteroarylalkyl, $OR_{12}$, and $NR_{13}R_{14}$;

$R_7$ is selected from $OR_{15}$, $SR_{15}$, S(O)$R_{16}$, $SO_2R_{17}$, $NR_{13}R_{14}$, and $NR_{12}SO_2R_6$;

$R_8$ is selected from H, $OR_{15}$, $NR_{13}R_{14}$, $C_1$-$C_6$ alkyl, $C_4$-$C_9$ cycloalkyl, $C_4$-$C_9$ heterocycloalkyl, aryl, heteroaryl, arylalkyl, and heteroarylalkyl;

$R_9$ is selected from $C_1$-$C_4$ alkyl and C(O)-alkyl;

$R_{10}$ and $R_{11}$ are the same or different and independently selected from H, $C_1$-$C_4$ alkyl, and —C(O)-alkyl;

$R_{12}$ is selected from H, $C_1$-$C_6$ alkyl, $C_4$-$C_9$ cycloalkyl, $C_4$-$C_9$ heterocycloalkyl, aryl, heteroaryl, arylalkyl, and heteroarylalkyl;

$R_{13}$ and $R_{14}$ are the same or different and independently selected from H, $C_1$-$C_6$ alkyl, $C_4$-$C_9$ cycloalkyl, $C_4$-$C_9$ heterocycloalkyl, aryl, heteroaryl, arylalkyl, heteroarylalkyl and amino acyl;

$R_{15}$ is selected from H, $C_1$-$C_6$ alkyl, $C_4$-$C_9$ cycloalkyl, $C_4$-$C_9$ heterocycloalkyl, aryl, heteroaryl, arylalkyl, heteroarylalkyl and $(CH_2)_mZR_{12}$;

$R_{16}$ is selected from $C_1$-$C_6$ alkyl, $C_4$-$C_9$ cycloalkyl, $C_4$-$C_9$ heterocycloalkyl, aryl, heteroaryl, arylalkyl, heteroarylalkyl and $(CH_2)_mZR_{12}$;

$R_{17}$ is selected from $C_1$-$C_6$ alkyl, $C_4$-$C_9$ cycloalkyl, $C_4$-$C_9$ heterocycloalkyl, aryl, heteroaryl, arylalkyl, heteroarylalkyl and $NR_{13}R_{14}$;

m is an integer selected from 0 to 6; and

Z is selected from O, $NR_{13}$, S, S(O), or a pharmaceutically acceptable salt thereof.

Useful compounds of the formula (II) include those wherein each of $R_1$, X, Y, $R_3$, and $R_4$ is H, including those wherein one of $n_2$ and $n_3$ is zero and the other is 1, especially those wherein $R_2$ is H or —$CH_2$—$CH_2$—OH.

One suitable genus of hydroxamate compounds are those of formula IIa

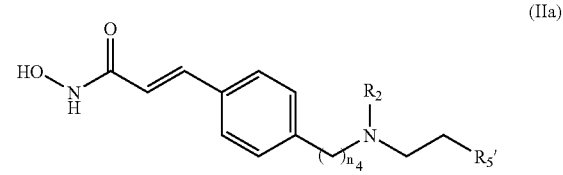

(IIa)

wherein $n_4$ is 0-3, $R_2$ is selected from H, $C_1$-$C_6$ alkyl, $C_4$-$C_9$ cycloalkyl, $C_4$-$C_9$ heterocycloalkyl, alkylcycloalkyl, aryl, heteroaryl, arylalkyl, heteroarylalkyl, —$(CH_2)_nC(O)R_6$, amino acyl and —$(CH_2)_nR_7$;

$R_5'$ is heteroaryl, heteroarylalkyl (e.g., pyridylmethyl), aromatic polycycles, non-aromatic polycycles, mixed aryl and non-aryl polycycles, polyheteroaryl, or mixed aryl and non-aryl polyheterocycles, or a pharmaceutically acceptable salt thereof.

Another suitable genus of hydroxamate compounds are those of formula IIa wherein $n_4$ is 0-3, $R_2$ is selected from H, $C_1$-$C_6$ alkyl, $C_4$-$C_9$ cycloalkyl, $C_4$-$C_9$ heterocycloalkyl, alkylcycloalkyl, aryl, heteroaryl, arylalkyl, heteroarylalkyl, —$(CH_2)_nC(O)R_6$, amino acyl and —$(CH_2)_nR_7$;

$R_5'$ is aryl, arylalkyl, aromatic polycycles, non-aromatic polycycles, and mixed aryl and non-aryl polycycles; especially aryl, such as p-fluorophenyl, p-chlorophenyl, p-O—$C_1$-$C_4$-alkylphenyl, such as p-methoxyphenyl, and p-$C_1$-$C_4$-alkylphenyl; and arylalkyl, such as benzyl, ortho, meta or para-fluorobenzyl, ortho, meta or para-chlorobenzyl, ortho, meta or para-mono, di or tri-O—$C_1$-$C_4$-alkylbenzyl, such as ortho, meta or para-methoxybenzyl, m,p-diethoxybenzyl, o,m,p-triimethoxybenzyl, and ortho, meta or para-mono, di or tri $C_1$-$C_4$-alkylphenyl, such as p-methyl, m,m-diethylphenyl, or a pharmaceutically acceptable salt thereof.

Another interesting genus are the compounds of formula IIb

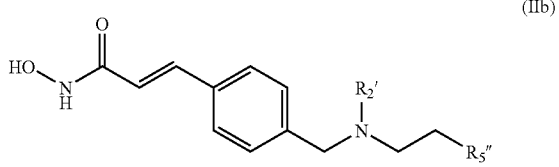

wherein $R_2'$ is selected from H, $C_1$-$C_6$ alkyl, $C_4$-$C_6$ cycloalkyl, cycloalkylalkyl (e.g., cyclopropylmethyl), $(CH_2)_{2-4}OR_{21}$ where $R_{21}$ is H, methyl, ethyl, propyl, and i-propyl, and $R_5''$ is unsubstituted 1H-indol-3-yl, benzofuran-3-yl or quinolin-3-yl, or substituted 1H-indol-3-yl, such as 5-fluoro-1H-indol-3-yl or 5-methoxy-1H-indol-3-yl, benzofuran-3-yl or quinolin-3-yl, or a pharmaceutically acceptable salt thereof.

Another interesting genus of hydroxamate HDAI compounds are the compounds of formula IIc

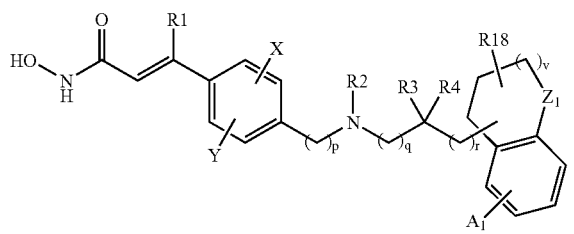

wherein the ring containing $Z_1$ is aromatic or non-aromatic, which non-aromatic rings are saturated or unsaturated, $Z_1$ is O, S or N—$R_{20}$, R18 is H, halo, $C_1$-$C_6$alkyl (methyl, ethyl, t-butyl), $C_3$-$C_7$cycloalkyl, aryl, for example unsubstituted phenyl or phenyl substituted by 4-$OCH_3$ or 4-$CF_3$, or heteroaryl, such as 2-furanyl, 2-thiophenyl or 2-, 3- or 4-pyridyl;

$R_{20}$ is H, $C_1$-$C_6$alkyl, $C_1$-$C_6$alkyl-$C_3$-$C_9$cycloalkyl (e.g., cyclopropylmethyl), aryl, heteroaryl, arylalkyl (e.g., benzyl), heteroarylalkyl (e.g., pyridylmethyl), acyl (acetyl, propionyl, benzoyl) or sulfonyl (methanesulfonyl, ethanesulfonyl, benzenesulfonyl, toluenesulfonyl)

$A_1$ is 1, 2 or 3 substituents which are independently H, $C_1$-$C_6$alkyl, —$OR_{19}$, halo, alkylamino, aminoalkyl, halo, or heteroarylalkyl (e.g., pyridylmethyl), $R_{19}$ is selected from H, $C_1$-$C_6$alkyl, $C_4$-$C_9$cycloalkyl, $C_4$-$C_9$heterocycloalkyl, aryl, heteroaryl, arylalkyl (e.g., benzyl), heteroarylalkyl (e.g., pyridylmethyl) and —$(CH_2CH=CH(CH_3)(CH_2))_{1-3}H$;

$R_2$ is selected from H, $C_1$-$C_6$ alkyl, $C_4$-$C_9$ cycloalkyl, $C_4$-$C_9$ heterocycloalkyl, alkylcycloalkyl, aryl, heteroaryl, arylalkyl, heteroarylalkyl, —$(CH_2)_nC(O)R_6$, amino acyl and —$(CH_2)_nR_7$;

v is 0, 1 or 2, p is 0-3, and q is 1-5 and r is 0 or q is 0 and r is 1-5, or a pharmaceutically acceptable salt thereof. The other variable substituents are as defined above.

Especially useful compounds of formula (IIc) are those wherein $R_2$ is H, or —$(CH_2)_pCH_2OH$, wherein p is 1-3, especially those wherein $R_1$ is H; such as those wherein $R_1$ is H and X and Y are each H, and wherein q is 1-3 and r is 0 or wherein q is 0 and r is 1-3, especially those wherein $Z_1$ is N—$R_{20}$. Among these compounds $R_2$ is preferably H or —$CH_2$—$CH_2$—OH and the sum of q and r is preferably 1.

Another useful genus of hydroxamate HDAI compounds are the compounds of formula IId

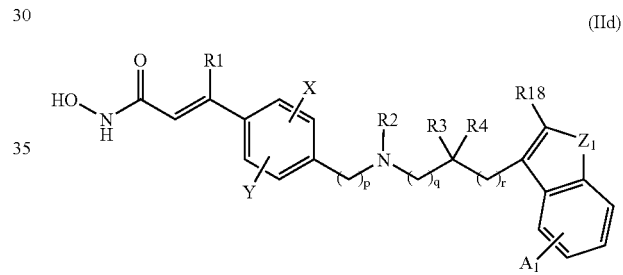

wherein $Z_1$ is O, S or N—$R_{20}$,

R18 is H, halo, $C_1$-$C_6$alkyl (methyl, ethyl, t-butyl), $C_3$-$C_7$cycloalkyl, aryl, for example, unsubstituted phenyl or phenyl substituted by 4-$OCH_3$ or 4-$CF_3$, or heteroaryl, $R_{20}$ is H, $C_1$-$C_6$alkyl, $C_1$-$C_6$alkyl-$C_9$cycloalkyl (e.g., cyclopropylmethyl), aryl, heteroaryl, arylalkyl (e.g., benzyl), heteroarylalkyl (e.g., pyridylmethyl), acyl (acetyl, propionyl, benzoyl) or sulfonyl (methanesulfonyl, ethanesulfonyl, benzenesulfonyl, toluenesulfonyl), $A_1$ is 1, 2 or 3 substituents which are independently H, $C_1$-$C_6$ alkyl, —$OR_{19}$, or halo, $R_{19}$ is selected from H, $C_1$-$C_6$alkyl, $C_4$-$C_9$-cycloalkyl, $C_4$-$C_9$heterocycloalkyl, aryl, heteroaryl, arylalkyl (e.g., benzyl), and heteroarylalkyl (e.g., pyridylmethyl);

p is 0-3, and q is 1-5 and r is 0 or q is 0 and r is 1-5, or a pharmaceutically acceptable salt thereof. The other variable substituents are as defined above.

Especially useful compounds of formula (IId) are those wherein $R_2$ is H, or —$(CH_2)_pCH_2OH$, wherein p is 1-3, especially those wherein $R_1$ is H; such as those wherein $R_1$ is H and X and Y are each H, and wherein q is 1-3 and r is 0 or wherein q is 0 and r is 1-3. Among these compounds R₂ is preferably H or —CH₂—CH₂—OH and the sum of q and r is preferably 1.

The present invention further relates to HDAI compounds of the formula IIe

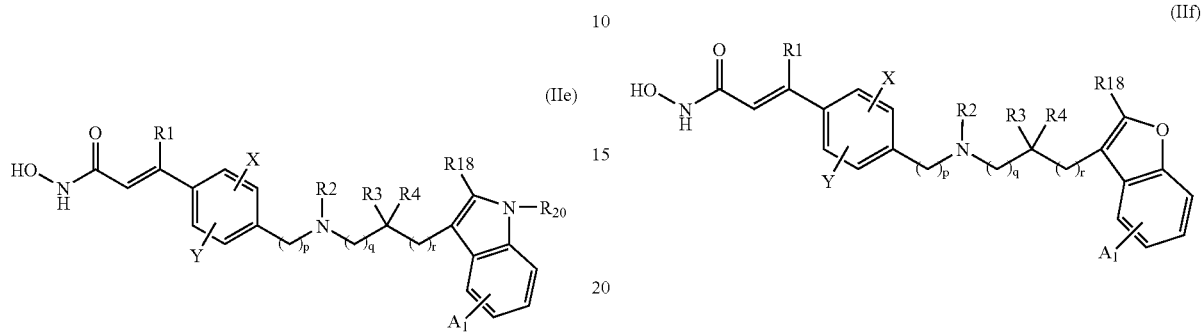

(IIe)

or a pharmaceutically acceptable salt thereof. The variable substituents are as defined above.

Especially useful compounds of formula (IIe) are those wherein R18 is H, fluoro, chloro, bromo, a $C_1$-$C_4$alkyl group, a substituted $C_1$-$C_4$alkyl group, a $C_3$-$C_7$cycloalkyl group, unsubstituted phenyl, phenyl substituted in the para position, or a heteroaryl (e.g., pyridyl) ring.

Another group of useful compounds of formula (IIe) are those wherein R₂ is H, or —(CH₂)$_p$CH₂OH, wherein p is 1-3, especially those wherein R₁ is H; such as those wherein R₁ is H and X and Y are each H, and wherein q is 1-3 and r is 0 or wherein q is 0 and r is 1-3. Among these compounds R₂ is preferably H or —CH₂—CH₂—OH and the sum of q and r is preferably 1.

Another group of useful compounds of formula (IIe) are those wherein R18 is H, methyl, ethyl, t-butyl, trifluoromethyl, cyclohexyl, phenyl, 4-methoxyphenyl, 4-trifluoromethylphenyl, 2-furanyl, 2-thiophenyl, or 2-, 3- or 4-pyridyl wherein the 2-furanyl, 2-thiophenyl and 2-, 3- or 4-pyridyl substituents are unsubstituted or substituted as described above for heteroaryl rings; R₂ is H, or —(CH₂)$_p$CH₂OH, wherein p is 1-3; especially those wherein R₁ is H and X and Y are each H, and wherein q is 1-3 and r is 0 or wherein q is 0 and r is 1-3. Among these compounds R₂ is preferably H or —CH—CH₂—OH and the sum of q and r is preferably 1.

Those compounds of formula IIe wherein R₂₀ is H or $C_1$-$C_6$alkyl, especially H, are important members of each of the subgenuses of compounds of formula IIe described above.

N-hydroxy-3-[4-[[(2-hydroxyethyl)[2-(1H-indol-3-yl)ethyl]-amino]methyl]phenyl]-2E-2-propenamide, N-hydroxy-3-[4-[[[2-(1H-indol-3-yl)ethyl]-amino]methyl]phenyl]-2E-2-propenamide and N-hydroxy-3-[4-[[[2-(2-methyl-1H-indol-3-yl)-ethyl]-amino]methyl]phenyl]-2E-2-propenamide, or a pharmaceutically acceptable salt thereof, are important compounds of formula (IIe).

The present invention further relates to the HDAI compounds of the formula IIf

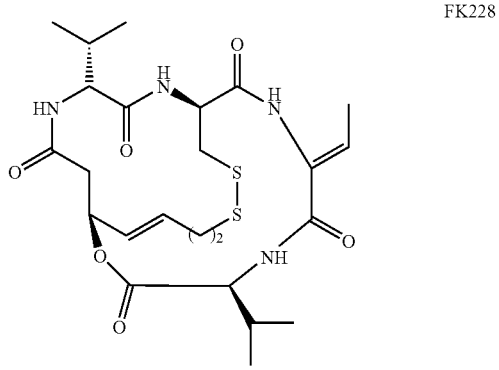

(IIf)

or a pharmaceutically acceptable salt thereof. The variable substituents are as defined above.

Useful compounds of formula (IIf) are include those wherein R₂ is H, or —(CH₂)$_p$CH₂OH, wherein p is 1-3, especially those wherein R₁ is H; such as those wherein R₁ is H and X and Y are each H, and wherein q is 1-3 and r is 0 or wherein q is 0 and r is 1-3. Among these compounds R₂ is preferably H or —CH₂—CH₂—OH and the sum of q and r is preferably 1.

N-hydroxy-3-[4-[[[2-(benzofur-3-yl)ethyl]-amino]methyl]phenyl]-2E-2-propenamide, or a pharmaceutically acceptable salt thereof, is an important compound of formula (IIf).

The above described HDAI compounds and the preparation thereof are described in WO 02/22577 published on Mar. 21, 2002. The specific HDAI compounds disclosed in WO 02/22577 are herein Incorporated by reference.

Other HDAI compounds useful in the practice of the present invention are for example Cl-994, the cyclic depsipeptide FK228 (formerly known as "FR901228"), MS-275 (formerly known as "MS-27-275"), SAHA, Sodium valproate, Pyroxamide, Phenyl butyrate, compounds 26 and 27, Prolifix and Apicidin (for chemical structures see below).

FK228

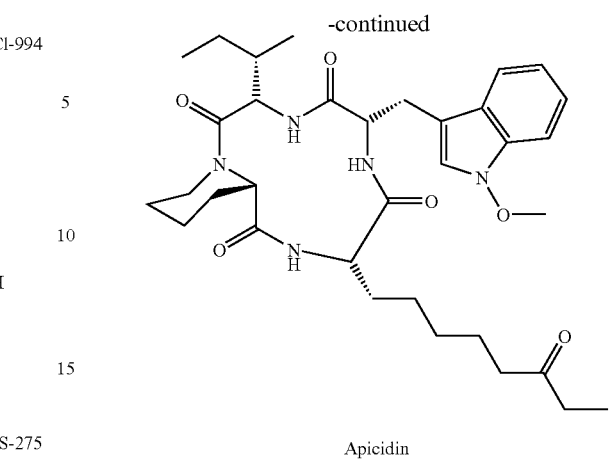
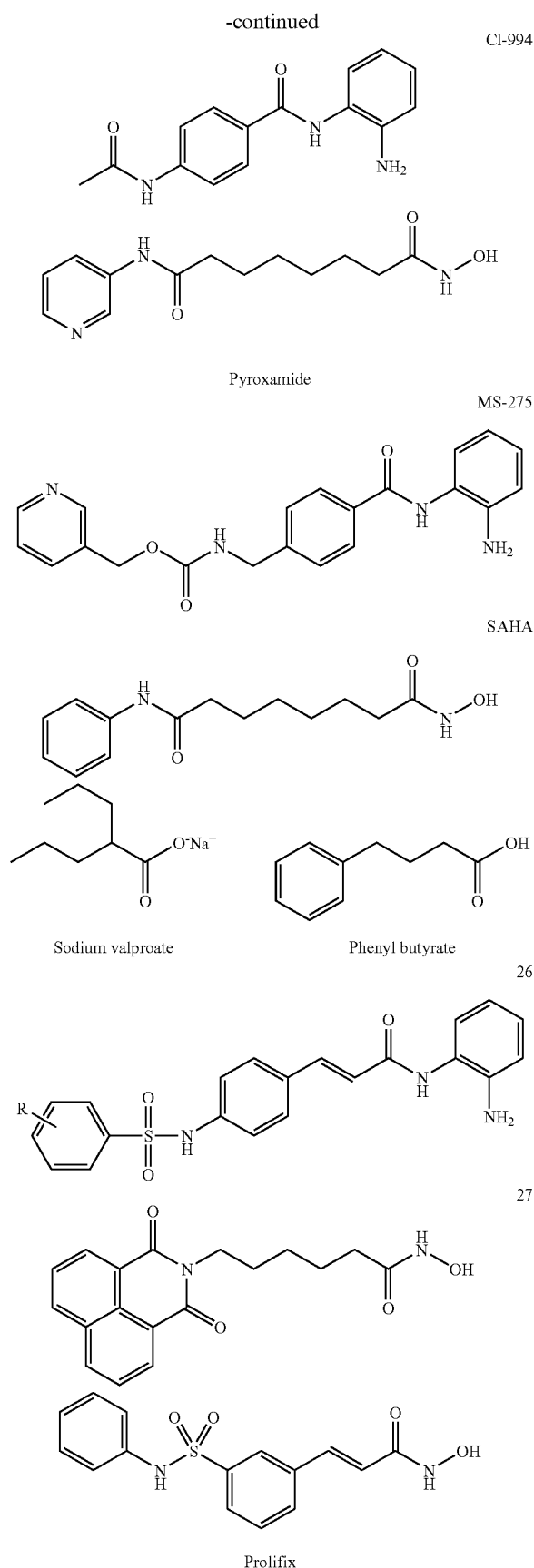

HDAI compounds used in the combination of the present invention are typically those which have an $IC_{50}$ of less than 2 μM, especially of less than 500 nM, and most preferably of less than 100 nM in the histone deacetylase inhibition assay described in Example B2 of WO 02/22577.

In a first aspect, the present invention relates to a combination, such as a combined preparation or a pharmaceutical composition, which comprises (a) a COX-2 inhibitor, especially the COX-2 inhibitors mentioned hereinbefore, In particular those mentioned as being preferred, and (b) an HDAI, especially the HDAIs mentioned hereinbefore, in particular those mentioned as being preferred, in which the active ingredients (a) and (b) are present in each case in free form or in the form of a pharmaceutically acceptable salt, for simultaneous, concurrent, separate or sequential use.

The term "a combined preparation" defines especially a "kit of parts" in the sense that the combination partners (a) and (b) as defined above can be dosed independently or by use of different fixed combinations with distinguished amounts of the combination partners (a) and (b), i.e., simultaneously, concurrently, separately or sequentially. The parts of the kit of parts can then, e.g., be administered simultaneously or chronologically staggered, that is at different time points and with equal or different time intervals for any part of the kit of parts. The ratio of the total amounts of the combination partner (a) to the combination partner (b) to be administered in the combined preparation can be varied, e.g. In order to cope with the needs of a patient sub-population to be treated or the needs of the single patient which different needs can be due to the particular disease, severity of the disease, age, sex, body weight, etc. of the patients.

Most preferably, the present invention relates to a combination of (a) a COX-2 inhibitor which is 5-methyl-2-(2'-chloro-6'-fluoro-anilino)-phenyl acetic acid, or a pharmaceutically acceptable salt thereof, and (b) an HDAI selected from the group consisting of N-hydroxy-3-[4-[[(2-hydroxyethyl)[2-(1H-indol-3-yl)ethyl]-amino]methyl]phenyl]-2E-2-propenamide, N-hydroxy-3-[4-[[[2-(1H-indol-3-yl)ethyl]-amino]methyl]phenyl]-2E-2-propenamide and N-hydroxy-3-[4-[[[2-(2-methyl-1H-indol-3-yl)-ethyl]-amino]methyl]phenyl]-2E-2-propenamide, and pharmaceutically acceptable salts thereof. Preferably, the HDAI is N-hydroxy-3-[4-[[(2-hydroxyethyl)[2-(1H-indol-3-yl)ethyl]-amino]methyl]phenyl]-2E-2-propenamide or a pharmaceutically acceptable salt thereof.

In a preferred embodiment, the present invention relates to a combination of the present invention for use in the treatment of a disease such as especially pre-malignant colon lesions or a colon cancer or other malignancies, preferably pre-malignant colon lesions or a colon cancer, in a mammal, particularly a human.

Other malignancies to be treated according to the present invention are preferably selected form the group consisting of breast cancer, lung cancer, ovarian cancer, lymphoma, head and neck cancer and cancer of the esophagus, stomach, bladder, prostrate, uterus and cervix.

In the context of the present invention the terms "treatment" or "treat" refer to both prophylactic or preventative treatment as well as curative or disease modifying treatment, including treatment of patients at risk of contracting the disease or suspected to have contracted the disease as well as patients who are ill or have been diagnosed as suffering from a disease or medical condition.

Within the context of this disclosure, any reference to a COX-2 Inhibitor or an HDAI is understood to include said compounds in their free form or as pharmaceutically acceptable salts or any crystal forms thereof including hydrates or solvates, if not indicated otherwise and where appropriate and expedient.

In another aspect, the present invention relates to the use of a COX-2 inhibitor, especially the COX-2 inhibitors mentioned hereinbefore, in particular those mentioned as being preferred, or a pharmaceutically acceptable salt thereof, for the preparation of a medicament, for use in combination with an HDAI, especially the HDAIs mentioned hereinbefore, in particular those mentioned as being preferred, or a pharmaceutically acceptable salt thereof, for the treatment of pre-malignant colon lesions or a colon cancer or other malignancies, preferably pre-malignant colon lesions or a colon cancer, in a mammal, particularly a human.

The present invention also relates to the use of an HDAI, especially the HDAIs mentioned hereinbefore, in particular those mentioned as being preferred, or a pharmaceutically acceptable salt thereof, for the preparation of a medicament, for use in combination with a COX-2 inhibitor, especially the COX-2 inhibitors mentioned hereinbefore, in particular those mentioned as being preferred, or a pharmaceutically acceptable salt thereof, for the treatment of pre-malignant colon lesions or a colon cancer or other malignancies, preferably pre-malignant colon lesions or a colon cancer, in a mammal, particularly a human.

In a further aspect, the present invention relates to pharmaceutical compositions comprising (a) one or more unit dosage forms of a COX-2 inhibitor, especially the COX-2 inhibitors mentioned hereinbefore, in particular those mentioned as being preferred, or a pharmaceutically acceptable salt thereof, and (b) one or more unit dosage forms of an HDAI, especially the HDAIs mentioned hereinbefore, in particular those mentioned as being preferred, or a pharmaceutically acceptable salt thereof, together with at least one pharmaceutically acceptable carrier.

The invention also relates to the use of a combination of the present invention for the preparation of a pharmaceutical composition for the treatment of pre-malignant colon lesions or colon cancer or other malignancies, preferably pre-malignant colon lesions or a colon cancer, in a mammal, particularly a human.

In another aspect, the present invention relates to a method of treating pre-malignant colon lesions or a colon cancer or other malignancies, preferably pre-malignant colon lesions or a colon cancer, in a mammal, particularly a human, which comprises treating the mammal simultaneously, concurrently, separately or sequentially with pharmaceutically effective amounts of (a) a COX-2 inhibitor, especially the COX-2 inhibitors mentioned hereinbefore, In particular those mentioned as being preferred, or a pharmaceutically acceptable salt thereof, and (b) an HDAI, especially the HDAIs mentioned hereinbefore, in particular those mentioned as being preferred, or a pharmaceutically acceptable salt thereof.

The present invention further relates to a commercial package or product comprising (a) a COX-2 inhibitor, especially the COX-2 inhibitors mentioned hereinbefore, in particular those mentioned as being preferred, or a pharmaceutically acceptable salt thereof, and (b) an HDAI, especially the HDAIs mentioned hereinbefore, in particular those mentioned as being preferred, or a pharmaceutically acceptable salt thereof, together with instructions for simultaneous, concurrent, separate or sequential use thereof in the treatment of a disease such as especially pre-malignant colon lesions or a colon cancer or other malignancies, preferably pre-malignant colon lesions or a colon cancer, in a mammal, particularly a human.

The present invention also relates to a commercial package or product comprising a COX-2 inhibitor, especially the COX-2 inhibitors mentioned hereinbefore, in particular those mentioned as being preferred, or a pharmaceutically acceptable salt thereof, together with instructions for use in combination with an HDAI, especially the HDAIs mentioned hereinbefore, in particular those mentioned as being preferred, or a pharmaceutically acceptable salt thereof, for the treatment of a disease such as especially pre-malignant colon lesions or a colon cancer or other malignancies, preferably pre-malignant colon lesions or a colon cancer, in a mammal, particularly a human, or a commercial package or product comprising an HDAI, especially the HDAIs mentioned hereinbefore, in particular those mentioned as being preferred, or a pharmaceutically acceptable salt thereof, together with instructions for use in combination with a COX-2 inhibitor, especially the COX-2 inhibitors mentioned hereinbefore, in particular those mentioned as being preferred, or a pharmaceutically acceptable salt thereof, for the treatment of a disease such as especially pre-malignant colon lesions or a colon cancer or other malignancies, preferably pre-malignant colon lesions or a colon cancer, in a mammal, particularly a human.

According to the present invention, a patient is treated with therapeutically effective amounts of a COX-2 inhibitor and an HDAI in order to treat pre-malignant colon lesions, such as polyps, or colon cancer, or another malignancy, each according to a dosage regimen that is appropriate for the individual agent. For example, the COX-2 inhibitor may be administered once or more daily and the HDAI may be administered once daily, on alternate days or on some other schedule—as is appropriate for the HDAI agent when used without the COX-2 inhibitor. One of skill in the art has the ability to determine appropriate pharmaceutically effective amounts of the combination components.

The COX-2 inhibitors and the HDAIs can be prepared and administered as described in the art such as in the documents cited above. If they are available on the market they can be administered for example in the form as marketed.

In the instance where the COX-2 inhibitor is 5-methyl-2-(2'-chloro-6'-fluoro-anilino)-phenyl acetic acid, or a pharmaceutically acceptable salt thereof, and the mammal is a human, an appropriate dose of 5-methyl-2-(2'-chloro-6'-fluoro-anilino)-phenyl acetic acid is in the range from 100 to 1500 mg daily, for example, 200-1000 mg/day, such as 200, 400, 500, 600, 800, 900 or 1000 mg/day, administered in one or two doses daily. Preferably, 5-methyl-2-(2'-chloro-6'-fluoro-anilino)-phenyl acetic acid, or a pharmaceutically acceptable salt thereof, is administered as an oral pharmaceutical formulation in the form of a tablet, capsule or syrup.

The following Examples illustrate the invention described above; they are not, however, intended to limit the scope of the invention in any way. The beneficial effects of the methods, compositions and combinations disclosed herein can also be determined by other test models known as such to the person skilled in the pertinent art.

EXAMPLES

The short forms and abbreviations used have the following definitions:
AcOH acetic acid
aq. aqueous
DMSO dimethyl sulfoxide
equiv. equivalent(s)
Et ethyl
EtOAc ethyl acetate
GC gas chromatography
HPLC high performance liquid chromatography
MeOH methanol
TFA trifluoroacetic acid
THF tetrahydrofuran

Example 1

Preparation of [2-(2'-chloro-6'-fluoro-phenylamino)-5-methyl-phenyl]acetic acid

A mixture of 20 g of 1-(2'-chloro-6'-fluorophenyl)-5-methyl-1,3-dihydro-indol-2-one, 266 ml of ethanol and 11 ml of water is heated to reflux. 24 g of a 30% solution of sodium hydroxide is slowly added and reflux is continued for 1 hour. The solution is cooled to 40-45° C. and treated slowly with a solution of 18 g of concentrated hydrochloric acid in 94 g of deionized water up to a pH of 3-4. The obtained suspension is cooled to 20-25° C. and the crystalline material is collected by filtration, washed with ethanol/deionized water and dried under reduced pressure to yield 19.5 g of pure [2-(2'-chloro-6'-fluoro-phenylamino)-5-methyl-phenyl]acetic acid. Melting point: 152-154° C.

$^1$H-NMR(DMSO-d$^6$, 500 MHz, 300K) δ 2.21 (s, 3H, CH$_3$), 3.64(s, 2H, CH$_2$); 6.42[dd, J=8.0 Hz, J$_{H-F}$=3.0, 1H, HC(6')], 6.90[dd, J=8.0, 2.0 Hz, 1H, HC(5)], 7.01[d, J=2.0 Hz, 1H, HC(3)], 7.09(s, 1H, NH), 7.09[ddd, J=8.5 Hz, J$_{H-F}$=5.5, 1H, HC(4')], 7.23[ddd, J=8.5, 1.5 Hz, J$_{H-F}$=11.0, 1H, HC(5')], 7.34[ddd, J=8.5, 1.5 Hz, J$_{H-F}$=1.5, 1H, HC(3')], 12.67(s, 1H, COOH).

Step 1.1A: Preparation of (2'-chloro-6'-fluorophenyl)-(4-methylphenyl)-amine 14.65 g (100 mmol) of 2-chloro-6-fluorophenol are dissolved in 50 ml of 2-propanol followed by the addition of 15.5 g (112 mmol) of potassium carbonate and 18.9 g (103 mmol) of 2-chloro-N-(4-methylphenyl)acetamide. The mixture is refluxed for 4 hours. At this time, the formation of 2-(2'-chloro-6'-fluorophenoxy)-N-(4-methylphenyl)acetamide is completed. 20 ml of sodium methylate solution 30% in methanol are slowly added. To maintain a temperature of at least 75° C., about 25 ml of solvent are distilled during the addition. The mixture is boiled 2 hours more to complete the formation of (2'-chloro-6'-fluorophenyl)-(4-methylphenyl)-amine.

Then 15 ml of solvent is distilled and 35 ml of water is added to obtain a two phases solution. The lower layer is discarded. The upper layer is diluted with 35 ml of heptane and washed with 3×25 ml of water. The organic phase is separated and concentrated in vacuo to obtain 21.8 g of crude oil (2'-chloro-6'-fluorophenyl)-(4-methylphenyl)-amine. This compound (HPLC purity 92%) is used without purification in the next step (Step 1.2). $^1$H-NMR (DMSO-d$^6$, 500 MHz, 300K) δ 2.17(s, 3H, CH$_3$); 6.53[dd, J=8.5 Hz, J$_{H-F}$=1.5, 2H, HC(2) and HC(6)], 6.94[d, J=8.0 Hz, 2H, HC(3) and HC(5)], 7.16[ddd, J=8.0 Hz, J$_{H-F}$=6.0, 1H, HC(4')], 7.25 [ddd, J=8.0, 1.5 Hz, J=8.0, 1H, HC(5')]; 7.34[ddd, J=8.0, 1.5 Hz, J$_{H-F}$=1.5, 1H, HC(3')]; 7.63(s, 1H, NH).

MS(EI) m/z 235 (100, M$^+$), 200 (35, (M-Cl)$^+$), 185 (55)

Preparation of starting material 2-chloro-6-fluorophenol

A solution of 12.1 g (108 mmol) of 2-fluorophenol, 70 mg of diisopropylamine and 400 ml of hexane-fraction is heated to 60-65° C.

4 g (56 mmol) of chlorine is introduced at this temperature. Then 60.5 g (540 mmol) of 2-fluorophenol are dropped in the solution over about 2 hours, while at the same rate 42 g (590 mmol) more chlorine is Introduced. After that 4 g more chlorine are introduced to complete the chlorination.

GC Check: 91% of 2-chloro-6-fluorophenol
5.2% of 4-chloro-6-fluorophenol
3.5% of 2,4-dichloro-6-fluorophenol 200-250 ml of solvent are distilled at normal pressure. The resulting concentrated solution is slowly cooled to 0-5° C. The obtained thick suspension is stirred at this temperature for 1 hour, washed with cold hexane-fraction and dried at room temperature.

Yield: 78 g white crystals. GC 99.7%. Melting point: 63.5-64.5° C.

MS(EI) m/z 146 (100, M$^+$), 126 [19, (M-HF)$^+$]

$^1$H-NMR(DMSO-d$^6$, 500 MHz, 300K) δ 6.8[ddd, J=8.2 Hz, J$_{H-F}$=5.5, 1H, HC(4)], 7.15 [m, 2H, HC(3) and HC(5)], 10.3(s, 1H, OH).

Preparation of starting material 2-chloro-N-(4-methylphenyl)acetamide

To a stirred mixture of 34.5 g (322 mmol) of p-toluidine, 100 ml of toluene and 100 ml of water are added at 20-25° C. from two separated dropping funnels 42.3 g (375 mmol) of chloroacetylchloride and 39 ml of concentrated sodium hydroxide 30% at such a rate to maintain a pH of 8-12. The obtained suspension is cooled to 0-5° C. The crystalline compound is filtered, washed with water and cold toluene and dried.

Yield: 55 g HPLC >99%.

Step 1.1B: Alternative preparation of (2'-chloro-6'-fluorophenyl)-(4-methylphenyl)-amine A mixture of 2-bromo-1-chloro-3-fluorobenzene (32 g, 153 mmol), p-toluidine (16.4 g, 153 mmol), sodium tert.butylate (27.5 g, 286 mmol), (±)-BINAP [2,2'-Bis-(diphenylphosphino)-1,1'-binaphthalin, 0.66 g, 1.1 mmol) and toluene (250 ml) is stirred under nitrogen for about 30 minutes. After the addition of Palladium-bis-(dibenzylideneaceton) (0.8 g, 1 mmol), the mixture is heated to 110° C. (slight reflux) for 14-20 hours. The mixture is then cooled to 30° C., water (60 ml), concentrated hydrochloric acid (60 ml) as well as charcoal and cellite (5 g each) are added and stirring is continued for an hour. The mixture is filtered and the filtrate is separated into the phases. The organic phase is washed with water (3 times, 70 ml each) and concentrated in vacuo to obtain 37.2 g of crude (2'-chloro-6'-fluorophenyl)-(4-methylphenyl)-amine. The product can be used in the next step (Step 1.2) as such; alternatively in can be kugelrohrdistilled in vacuo.

Step 1.1C: Alternative preparation of (2'-chloro-6'-fluorophenyl(4-methylphenyl)-amine A mixture of 2-chloro-6-fluoroaniline (4.00 g, 27.5 mmol), 4-bromotoluene (4.70 g, 27.5 mmol), sodium tert-butylate (4.75 g, 49.4 mmol), and toluene (55 mL) is stirred at 25° C. under nitrogen for 30 minutes. To this mixture, a solution of palladium-bis-(dibenzylideneacetone) (15.8 mg, 55 mmol) and tri-tert-butylphosphine (1) (8.3 mg, 0.04 mmol) in toluene (5 mL) is added and the resulting suspension is stirred at 110° C. for 14 hours. The mixture is then cooled to 30° C. Water (30 ml), concentrated hydrochloric acid (10 ml), charcoal and cellite (1 g each) are added and stirring is continued for 1 hour. The mixture is filtered and the filtrate is separated into its phases. The organic phase is washed three times with water (10 mL) and concentrated in vacuo to give 6.5 g of crude (2'-chloro-6'-fluorophenyl)-(4-methylphenyl)-amine. The product can be used directly in the next step (Step 1.2). Alternatively, it can be distilled in vacuo by Kugelrohr.

Step 1.2: Preparation of 2-chloro-N-(2'-chloro-6'-fluorophenyl)-N-(4-methylphenyl) acetamide 20.4 g of crude (2'-chloro-6'-fluorophenyl)-(4-methylphenyl)-amine are heated to about 80° C. and treated with 10.75 g of chloroacetylchloride. The mixture is stirred for 2 hours and diluted with 10 ml of 2-propanol. The solution is cooled to 35-40° C. and seeded. The precipitated suspension is diluted with 30 ml of hexane, cooled to 0-5° C. and stirred for about 1 hour. The crystals are isolated by filtration, washed with a cold solution of 2-propanol/hexane ⅓. After drying, 22.7 g of 2-chloro-N-(2'-chloro-6'-fluorophenyl)-N-(4-methylphenyl)acetamide are obtained. HPLC purity: 99%. Melting point: 79-80° C. $^1$H-NMR(DMF-d$^7$, 400 MHz, 393K) δ 2.44(s, 3H, CH$_3$); 4.32 (s, 2H, CH$_2$), 7.35[d, J=8.0 Hz, 2H, HC(3) and HC(5)], 7.43[ddd, J=8.0, 2.0 Hz, $J_{H-F}$=8.0, 1H, HC(5')], 7.48[d, J=8.0 Hz, 2H, HC(2) and HC(6)], 7.55[d, J=8.0 Hz, 1H, HC(3')], 7.60[ddd, J=8.0 Hz, $J_{H-F}$=5.5, 1H, HC(4')].

Step 1.3: Preparation of 1-(2'-Chloro-6'-fluorophenyl)-5-methyl-1,3-dihydro-indol-2-one A melt of 124.8 g (400 mmol) of 2-chloro-N-(2'-chloro-6'-fluorophenyl)-N-(4-methylphenyl)acetamide at 100-120° C. is treated with 69.3 g (520 mmol) of aluminium chloride in small parts. The mixture is heated to 160° C. and stirred for 4-6 hours at this temperature.

The molten mixture is cooled to 110° C. and diluted with 300 ml of toluene. The obtained solution is added to 500 ml of water at 60° C. The organic phase is separated while hot, decolorized with activated carbon, filtered and concentrated. The residue is dissolved in hot 2-propanol, decolorized again with activated carbon, filtered and concentrated to a volume of about 250 ml. The obtained suspension is cooled to 0-5° C., filtered, washed with cold 2-propanol. After drying, 87 g of 1-(2'-chloro-6'-fluorophenyl)-5-methyl-1,3-dihydro-indol-2-one are obtained. Melting point: 137.5-138.5° C.

$^1$H-NMR(DMSO-d$^6$, 500 MHz, 300K) δ 2.27(s, 3H, CH$_3$); 3.83(s, 2H, CH$_2$); 6.35[d, J=8.0 Hz, 1H, HC(7)], 7.01 [d, J=8.0 Hz, 1H, HC(6)], 7.19[s, 1H, CH(4)], 7.52[ddd, J=8.5, 2.0 Hz, $J_{H-F}$=10.0, 1H, HC(5')], 7.60[ddd, J=8.5, 2.0 Hz, $J_{H-F}$=1.5, 1H, HC(3')], 7.63[ddd, J=8.5 Hz, $J_{H-F}$=1.5, 1H, HC(4')].

Example 2

Preparation of N-Hydroxy-3-[4-[[[2-(1H-indol-3-yl)-ethyl]-amino]methyl]phenyl]-2E-2-propenamide 4-Formylcinnamic acid methylester is produced by adding 4-formylcinnamic acid (25 g, 0.143 mol) in MeOH and HCl (6.7 g, 0.18 mol). The resulting suspension is heated to reflux for 3 hours, cooled and evaporated to dryness. The resulting yellow solid is dissolved In EtOAc, the solution washed with saturated NaHCO$_3$, dried (MgSO$_4$) and evaporated to give a pale yellow solid which is used without further purification (25.0 g, 92%). To a solution of tryptamine (16.3 g, 100 mmol) and 4-formylcinnamic acid methylester (19 g, 100 mmol) in dichloroethane, NaBH(OAc)$_3$ (21 g, 100 mmol) is added. After 4 hours the mixture is diluted with 10% K$_2$CO$_3$ solution, the organic phase separated and the aqueous solution extracted with CH$_2$Cl$_2$. The combined organic extracts are dried (Na$_2$SO$_4$), evaporated and the residue purified by flash chromatography to produce 3-(4-{[2-(1H-indol-3-yl)-ethylamino]-methyl}-phenyl)-(2E)-2-propenoic acid methyl ester (29 g). A solution of KOH (12.9 g 87%, 0.2 mol) in MeOH (100 mL) is added to a solution of HONH$_2$.HCl (13.9 g, 0.2 mol) in MeOH (200 mL) and a precipitate results. After 15 minutes the mixture is filtered, the filter cake washed with MeOH and the filtrate evaporated under vacuum to approximately 75 mL. The mixture is filtered arm the volume adjusted to 100 mL with MeOH. The resulting solution 2M HONH$_2$ is stored under N$_2$ at −20° C. for up to 2 weeks. Then 3-(4-{[2-(1H-indol-3-yl)-ethylamino]-methyl}phenyl)-(2E)-2-propenoic acid methyl ester (2.20 g, 6.50 mmol) is added to 2 M HONH$_2$ in MeOH (30 mL, 60 mmol) followed by a solution of KOH (420 mg, 6.5 mmol) in MeOH (5 mL). After 2 hours dry ice is added to the reaction and the mixture is evaporated to dryness. The residue is dissolved in hot MeOH (20 mL), cooled and stored at −20° C. overnight. The resulting suspension is filtered, the solids washed with ice cold MeOH and dried under vacuum, producing N-Hydroxy-3-[4-[[[2-(1H-indol-3-yl)-ethyl]-amino]methyl]phenyl]-2E-2-propenamide (m/z 336 [MH$^+$]).

Example 3

Preparation of N-Hydroxy-3-[4-[[(2-hydroxyethyl)[2-(1H-indol-3-yl)-ethyl]-amino]methyl]phenyl]-2E-2-propenamide A solution of 3-(4-{[2-(1H-indol-3-yl)-ethylamino]-methyl}-phenyl)-(2E)-2-propenoic acid methyl ester (12.6 g, 37.7 mmol), (2-bromoethoxy)-tert-butyldimethylsilane (12.8 g, 53.6 mmol), (i-Pr)$_2$NEt, (7.42 g, 57.4 mmol) in DMSO (100 mL) is heated to 50° C. After 8 hours the mixture is partitioned with CH$_2$Cl$_2$/H$_2$O. The organic layer is dried (Na$_2$SO$_4$) and evaporated. The residue is chromatographed on silica gel to produce 3-[4-({[2-(tert-butyldimethylsilanyloxy)-ethyl]-[2-(1H-indol-3-yl)-ethyl]-amino}-methyl)-phenyl]-(2E)-2-propenoic acid methyl ester (13.1 g). A solution of KOH (12.9 g (87% pure), 0.2 mol) in MeOH (100 mL) is added to a solution of HONH$_2$.HCl (13.9 g, 0.2 mol) in MeOH (200 mL) and a precipitate results. After 15 minutes the mixture is filtered, the filter cake washed with MeOH and the filtrate evaporated under vacuum to approximately 75 mL. The mixture is filtered and the volume adjusted to 100 mL with MeOH. The resulting solution 2M HONH$_2$ is stored under N$_2$ at −20° C. for up to 2 weeks. Then 3-[4-({[2-(tert-butyldimethylsilanyloxy)-ethyl]-[2-(1H-indol-3-yl)-ethyl]-amino}-methyl)-phenyl]-(2E)-2-propenoic acid methyl ester (5.4 g, 11 mmol) is added to 2 M HONH$_2$ in MeOH (90 mL, 180 mmol) followed by a solution of KOH (720 mg (87% pure), 11.2 mmol) in MeOH (5 mL) and the mixture stirred overnight. Dry ice is added to the reaction and the mixture diluted with H$_2$O resulting in the formation of a precipitate. The liquid was decanted and the solid was dissolved in MeOH and filtered. The filtrate is evaporated to afford N-hydroxy-3-[4-({[2-(tert-butyldimethylsilanyloxy)-ethyl]-[2-(1H-indol-3-yl)-ethyl]-amino}methyl)-phenyl]-(2E)-2-propenamide (5.1 g,) which is used without further purification. The hydroxamic acid (5.0 g, 13.3 mmol) is then dissolved in 95% TFA/H$_2$O (59 mL) and heated to 40-50° C. for 4 hours. The mixture is evaporated and the residue purified by reverse phase HPLC to produce N-Hydroxy-3-[4-[[(2-hydroxyethyl)[2-(1H-indol-3-yl)-ethyl]-amino]methyl]phenyl]-2E-2-propenamide as the trifluoroacetate salt (m/z 380 [MH$^+$]).

Example 4

Preparation of N-hydroxy-3-[4-[[[2-(2-methyl-1H-indol-3-yl)-ethyl]-amino]methyl]phenyl]-2E-2-propenamide A suspension of LiAlH$_4$ (17 g, 445 mmol) in dry THF (1000 mL) is cooled to 0° C. and 2-methylindole-3-glyoxylamide (30 g, 148 mmol) is added in portions over 30 minutes. The mixture is stirred at room temperature for 30 minutes and then maintained at reflux for 3 hours. The reaction is cooled to 0° C. and treated with H$_2$O (17 ml), 15% NaOH (aq., 17 ml) and H$_2$O (51 ml). The mixture is treated with MgSO$_4$, filtered and the filtrate evaporated to give 2-methyltryptamine which is dissolved in MeOH. Methyl 4-formylcinnamate (16.9 g, 88.8 mmol) is added to the solution, followed by NaBH$_3$CN (8.4 g) and AcOH (1 equiv.). After 1 hour the reaction is diluted with NaHCO$_3$ (aq.) and extracted with EtOAc. The organic extracts are dried (MgSO$_4$), filtered and evaporated. The residue is purified by chromatography to give 3-(4-{[2-(2-methyl-1H-indol-3-yl)-ethylamino]-methyl}-phenyl)-(2E)-2-propenoic acid methyl ester. The ester is dissolved in MeOH, 1.0 M HCl/dioxane (1-1.5 equiv.) is added followed by Et$_2$O. The resulting precipitate is filtered and the solid washed with Et$_2$O and dried thoroughly to give 3-(4-{[2-(2-methyl-1H-indol-3-yl)-ethylamino]-methyl}-phenyl)-(2E)-2-propenoic acid methyl ester hydrochloride. 1.0 M NaOH (aq., 85 mL) is added to an ice cold solution of the methyl ester hydrochloride (14.9 g, 38.6 mmol) and HONH$_2$ (50% aq. solution, 24.0 mL, ca. 391.2 mmol). After 6 hours, the ice cold solution is diluted with H$_2$O and NH$_4$Cl (aq., 0.86 M, 100 mL). The resulting precipitate is filtered, washed with H$_2$O and dried to afford N-hydroxy-3-[4-[[[2-(2-methyl-1H-indol-3-yl)-ethyl]-amino]methyl]phenyl]-2E-2-propenamide (m/z 350 [MH$^+$]).

Example 5

5-methyl-2-(2'-chloro-6'-fluoro-anilino)-phenyl acetic acid (alternatively named [2-(2'-chloro-6'-fluoro-phenylamino)-5-methyl-phenyl]acetic acid; for the preparation see Example 1) ("COX") and N-hydroxy-3-[4-[[(2-hydroxyethyl)[2-(1H-indol-3-yl)ethyl]-amino]methyl]phenyl]-2E-2-propenamide (alternatively named (E)-N-Hydroxy-3-[4-({(2-hydroxy-ethyl)-[2-(1H-indol-3-yl)-ethyl]-amino}-methyl)-phenyl]-acrylamide; for the preparation see Example 3) ("HDAI") are tested as single agents and together as combination therapy in a mouse model of adenomatous polyposis for the prevention and treatment of intestinal polyps. HDAI is administered intravenously to the mice at 10 mg/kg in a 5% (w/v) dextrose in water solution, q.d., 3 times per week for three weeks. COX is administered as a dietary admixture at a concentration of 125 ppm. % T/C is the quotient of the mean number of polyps in the treated mice divided by the mean number of polyps in the control mice times 100. The following results of duplicate experiments are observed:

| DRUGS | | | | POLYPS | | ANIMALS | |
| --- | --- | --- | --- | --- | --- | --- | --- |
| Compound | Route | Regimen | Dose (mg/kg) | Mean Intestinal Polyp Count (# ± SEM) | % T/C | % Body Wt. Change | Dead/Total |
| Control | feed | ad libitum | — | 23 ± 2.0 | — | +8.2 ± 0.1 | 0/4 |
| COX | feed | ad libitum | 125 ppm | 14 ± 0.7 | 60 | +10 ± 0.1 | 0/7 |
| HDAI | i.v. | 3x/wk | 10 mg/kg | 12 ± 0.57 | 52 | +3.5 ± 0.1 | 0/7 |
| COX + HDAI | feed + i.v | ad libitum + 3x/wk | 125 ppm + 10 mg/kg | 8 ± 0.27 | 33 | +4.8 ± 0.1 | 0/7 |
| Control | feed | ad libitum | — | 26 ± 0.4 | — | +16.3 ± 0.2 | 0/4 |
| COX | feed | ad libitum | 125 ppm | 12 ± 0.3 | 46 | +8.1 ± 0.2 | 0/7 |
| HDAI | i.v. | 3x/wk | 10 mg/kg | 15 ± 0.3 | 57 | +9.6 ± 0.1 | 0/7 |
| COX + HDAI | feed + i.v | ad libitum + 3x/wk | 125 ppm + 10 mg/kg | 8 ± 0.3 | 30 | +6.7 ± 0.1 | 0/7 |

Both agents alone cause a statistically significant reduction in the number of newly formed intestinal polyps. The combination further reduces the number of polyps to a level that is statistically significantly lower than the number of polyps obtained by treatment with either agent alone. Statistical evaluations are performed using a one tailed Student t-test and all p values are less than 0.01.

What is claimed is:

1. A combination which comprises (a) a pharmaceutically effective amount of 5-methyl-2-(2'-chloro-6'-fluoro-anilino)-phenyl acetic acid, or a pharmaceutically acceptable salt thereof, and (b) a pharmaceutically effective amount of N-hydroxy-3[4-[{(2-hydroxyethyl)[2-(1H-indol-3-yl)ethyl]-amino]methyl}phenyl)-2E-2-propenamide, or a pharmaceutically acceptable salt thereof, for use in the treatment of pre-malignant colon lesions or colon cancer in a mammal.

* * * * *